(12) United States Patent
Martin et al.

(10) Patent No.: US 9,903,836 B2
(45) Date of Patent: Feb. 27, 2018

(54) MICROFLUIDIC DEVICES AND METHODS FOR FABRICATING MICROFLUIDIC DEVICES

(71) Applicant: Saint Louis University, St. Louis, MO (US)

(72) Inventors: Robert Scott Martin, Kirkwood, MO (US); Asmira Selmovic Alagic, St. Louis, MO (US); Alicia Johnson Hoover, Webster Groves, MO (US)

(73) Assignee: Saint Louis University, St. Louis, MO (US)

( * ) Notice: Subject to any disclaimer, the term of this patent is extended or adjusted under 35 U.S.C. 154(b) by 308 days.

(21) Appl. No.: 14/309,307

(22) Filed: Jun. 19, 2014

(65) Prior Publication Data

US 2015/0001083 A1 Jan. 1, 2015

Related U.S. Application Data

(60) Provisional application No. 61/840,235, filed on Jun. 27, 2013.

(51) Int. Cl.
| | |
|---|---|
| *C02F 1/40* | (2006.01) |
| *B01L 3/00* | (2006.01) |
| *G01N 27/447* | (2006.01) |
| *B29K 63/00* | (2006.01) |
| *B29L 31/00* | (2006.01) |
| *B29C 35/02* | (2006.01) |

(52) U.S. Cl.
CPC .. *G01N 27/44791* (2013.01); *B01L 3/502707* (2013.01); *B01L 3/502715* (2013.01); *B01L 2300/088* (2013.01); *B01L 2300/0816* (2013.01); *B01L 2300/0838* (2013.01); *B01L 2400/0421* (2013.01); *B29C 35/02* (2013.01); *B29K 2063/00* (2013.01); *B29L 2031/752* (2013.01)

(58) Field of Classification Search
USPC ................... 422/502–504; 204/601
See application file for complete search history.

(56) References Cited

U.S. PATENT DOCUMENTS

| | | | |
|---|---|---|---|
| 6,444,173 B1 * | 9/2002 | Sjursen ................ | B01L 3/0268 204/600 |
| 2009/0253181 A1 * | 10/2009 | Vangbo ............ | G01N 27/44791 435/91.1 |
| 2009/0321356 A1 * | 12/2009 | Gerhardt .............. | G01N 30/606 210/656 |
| 2016/0018347 A1 * | 1/2016 | Drbal ..................... | A61M 1/28 210/647 |

* cited by examiner

*Primary Examiner* — Dean Kwak
(74) *Attorney, Agent, or Firm* — Stinson Leonard Street LLP

(57) ABSTRACT

The present disclosure relates generally to microfluidic devices and methods for fabricating the devices. More particularly, the present disclosure relates to microfluidic devices having encapsulated fluidic tubing and encapsulated electrodes, microfluidic devices having encapsulated fluidic tubing, encapsulated capillary loops and encapsulated electrodes, and methods of fabricating devices having encapsulated fluidic tubing, encapsulated capillary loops and encapsulated electrodes resulting in reduced dead volume interconnects between the fluidic tubing and capillary loops and associated microchannels and aligned fluidic tubing openings, capillary loop openings, electrodes and other device features.

5 Claims, 18 Drawing Sheets

In Tubing   8.3 ± 1.7 nL

On Chip   10.5 ± 1.6 nL

In Tubing   5.7 ± 0.8 nL

On Chip   32.9 ± 7.7 nL

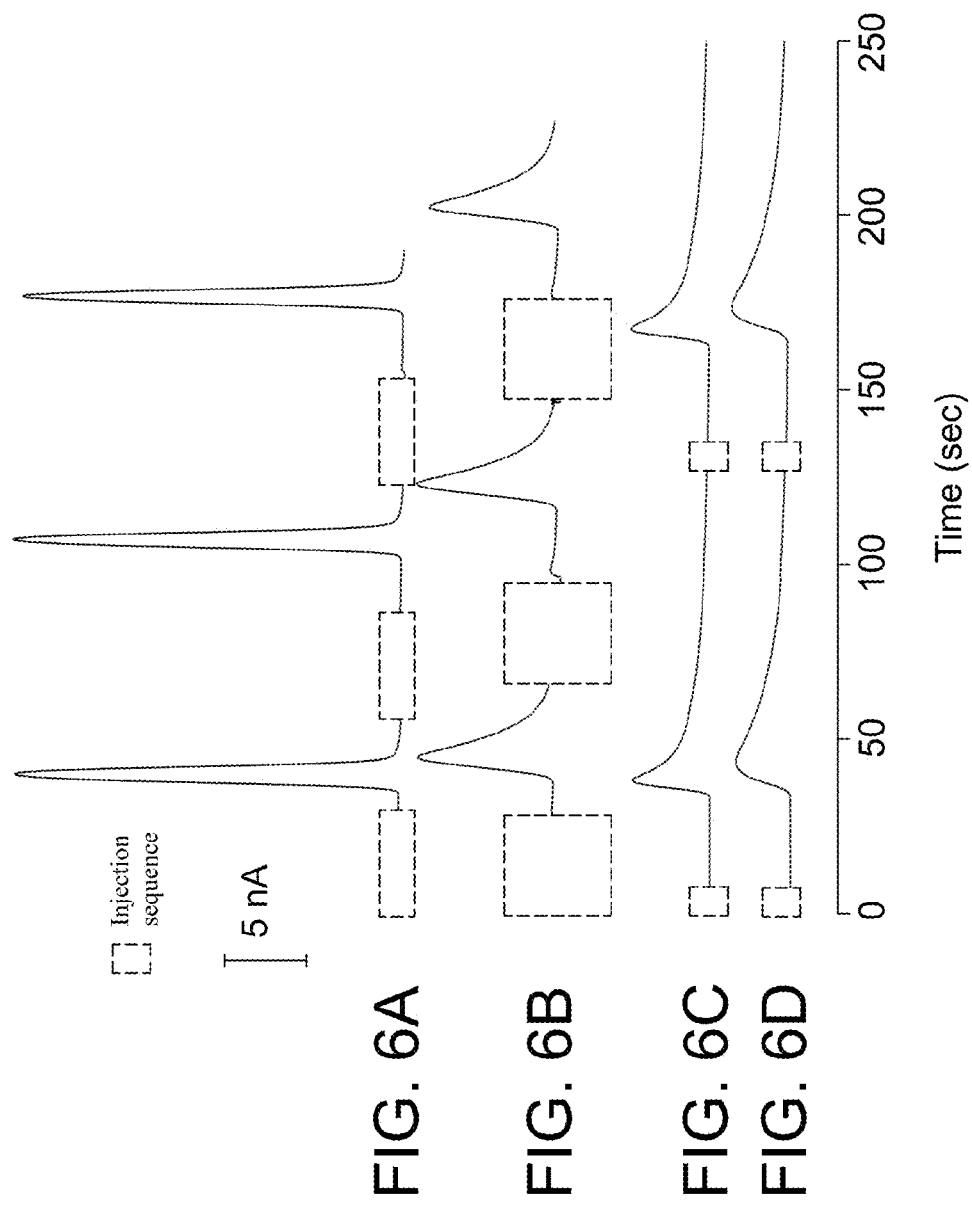

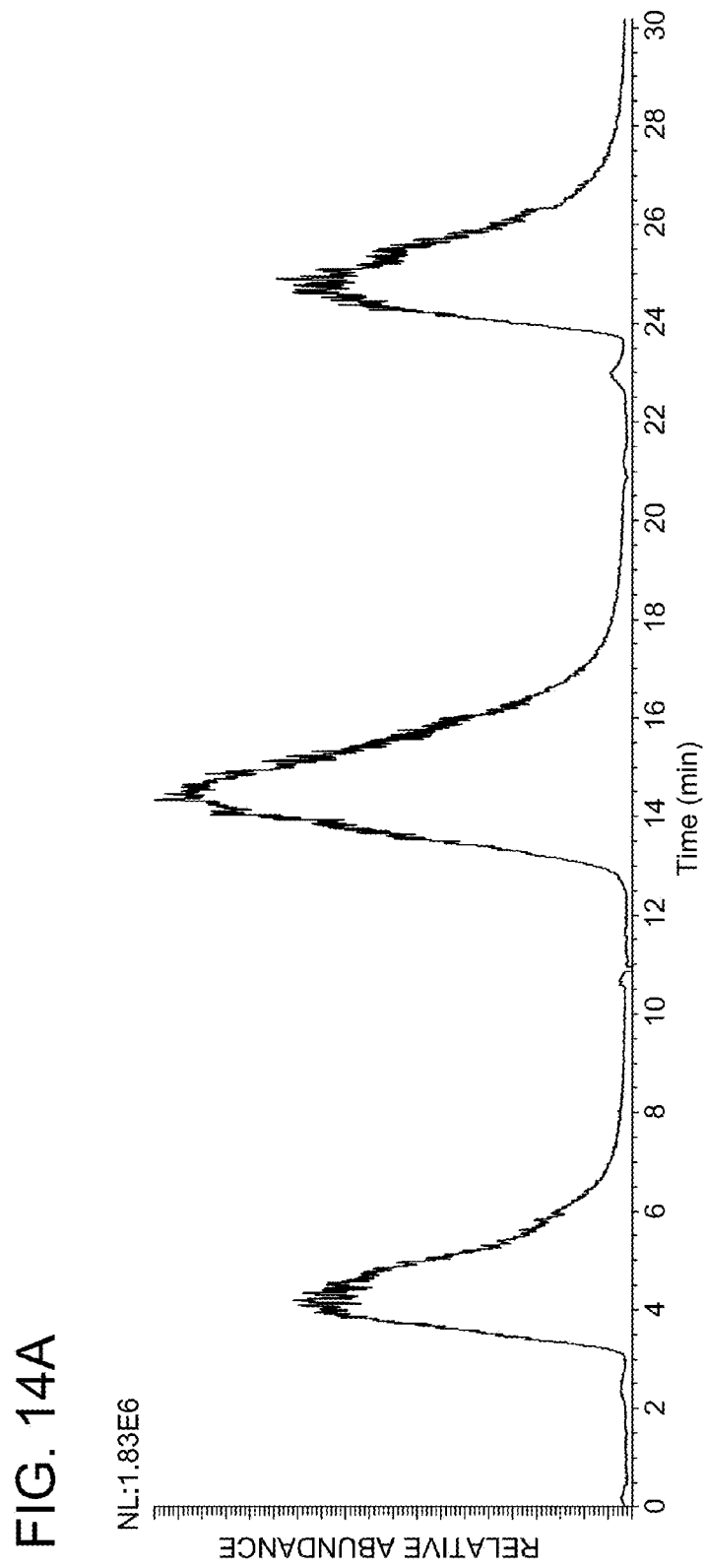

MICROFLUIDIC DEVICES AND METHODS FOR FABRICATING MICROFLUIDIC DEVICES

CROSS REFERENCE TO RELATED APPLICATIONS

This application claims priority to U.S. Ser. No. 61/840,235, filed on Jun. 27, 2013, which is incorporated by reference herein in its entirety.

STATEMENT REGARDING FEDERALLY SPONSORED RESEARCH OR DEVELOPMENT

This invention was made with government support under Grant Award No. R15GM084470-03 awarded by the National Institute of General Medical Sciences of the National Institutes of Health. The government has certain rights in the invention.

BACKGROUND OF THE DISCLOSURE

The present disclosure relates generally to microfluidic devices and methods for fabricating the microfluidic devices. More particularly, the present disclosure relates to microfluidic devices and methods for fabricating microfluidic devices having encapsulated fluidic tubing and encapsulated electrodes. The microfluidic devices and methods for fabricating the microfluidic devices of the present disclosure provide stronger and more robust microfluidic devices and have stable fluidic interconnects with reduced or no dead volume at the fluidic interconnects. The microfluidic devices and methods for fabricating the microfluidic devices of the present disclosure also allow for coplanar alignment of the fluidic tubing, electrodes and other device features.

Microfluidic device (also referred to herein as microchips) systems are becoming widely used analytical tools for a variety of applications. There are numerous advantages of these systems, one of which is the integration of multiple processes. This can include coupling off-chip processes to the microchip devices as well as integrating multiple processes on-chip. Using microfluidic devices for these types of integration can result in minimal dilution, fast analysis, and improved temporal resolution so that changes in analyte concentration can be monitored in close to real-time. There are numerous examples of integrating multiple processes with microfluidic devices. For example, some processes integrated with microfluidic devices can include coupling conventional capillary electrophoresis (CE) with microfabricated cell traps for single cell analysis, combining capillary liquid chromatography with on-chip CE and electrospray ionization, integrating microdialysis sampling with microchip-based analysis, using multi-layer microfluidic devices for integrating cell culture with analysis, integrating flowing red blood cells, cultured endothelial cells, and electrodes for measuring transendothelial electrical resistance, and the coupling of digital microfluidic devices with mass spectrometry detection.

Integrating off-chip processes to the microchip devices includes fabricating microchip devices with electrodes, fluidic tubing and other features such as, for example, valving techniques, pipettors, discrete injections, plate readers, and off-chip detectors. It has been demonstrated that electrodes can be integrated with microfluidic devices by encapsulating electrodes in epoxy to form an electrode base. The resulting electrode base can be coupled with a polydimethylsiloxane (PDMS) layer to form a microfluidic device. A 3-dimensional arrangement of the electrodes can be created in such a device, and multiple electrode materials can be used to integrate microchip electrophoresis with electrochemical detection.

Another method for making electrodes for microfluidic devices is to create an electrode base via sputtering of metal materials and traditional photolithography. These are typically termed "thin layer electrodes" and are ~0.1 microns in height. The types of materials that can be made this way are usually limited to just gold or platinum and generally have a very small surface area that limits their analytical performance.

Fluidic tubing can also be integrated with the devices by inserting the fluidic tubing into the epoxy base layer or through a top layer made from soft material such as PDMS to form a fluid interconnect between the fluidic tubing and the microchannel of the microfluidic device. Integration of the fluidic tubing with the microchannel to form the fluid interconnect, however, results in an increased dead volume because of the portion of fluidic tubing that extends or protrudes into the microchannel. The manner with which the fluidic tubing is interfaced with the microchannel can significantly affect integrating off-chip processes with the microchip because of the dead volume created by the fluidic tubing-microchannel interface. For continuous flow processes, the dead volume associated with the fluidic tubing connection may not be crucial. But, in cases where dilution effects are an issue, such as where the analyte concentration rapidly changes as a function of time, when high temporal measurements are desired, or when the sample volume is limited, the fluidic tubing-microchannel interface connection becomes a factor.

One method of coupling fluidic tubing with a microchip involves inserting the tubing into or onto the outer surface of the device, such as through a PDMS layer, and positioning the fluidic tubing outlet into a microchannel of the PDMS layer. However, the amount of dead volume with this type of connection can vary depending upon how far the fluidic tubing is pressed into the device and/or the size of the hole used to interface with the microchannel. Further, because PDMS is a soft material, this type of inserted connection is not very stable. For example, the PDMS material can be damaged during insertion of the fluidic tubing, such as by inadvertent contact with the fluidic tubing, or the fluidic tubing outlet can become inadvertently repositioned within the microchannel, or pulled out of the microchannel entirely. Any such perturbation to the fluidic tubing can also cause leakage or cause the microchip to no longer be sealed, resulting in fluid leaks.

Another method of coupling fluidic tubing that has been used is inserting tubing into the side of the microchip, where the fluidic tubing is butted flush with the microchannel. While this has been shown to result in low dead volume interconnects, fabrication of the device is not trivial. For both methods, there are often issues with the stability of the fluidic tubing-microchannel connection, and complexity of the device increases when multiple fluidic tubing interconnects are needed.

Accordingly, there is a need for microfluidic devices and methods of fabricating microfluidic devices. The microfluidic devices and methods of the present disclosure advantageously include fluidic tubing having stable fluidic interconnects and a reduced or no dead volume. The microfluidic devices and methods of the present disclosure also advantageously allow for alignment of the fluidic tubing, electrodes and other device features along the same plane of the device. Further, base layers can be polished to result in a flat surface that makes bonding with a microchannel layer more robust. Since the alignment can be fixed and the fluidic tubing, electrodes and other device features are encapsulated in the same base layer, connections are straightforward and originate from the same side of the device, which can be critical for high throughput, automation studies.

SUMMARY OF THE DISCLOSURE

The present disclosure relates generally to microfluidic devices and methods for fabricating the microfluidic devices. More particularly, the present disclosure relates to microfluidic devices and methods for fabricating microfluidic devices having encapsulated fluidic tubing, encapsulated electrodes and other device features. The microfluidic devices and methods for fabricating the microfluidic devices of the present disclosure make possible the alignment of the tubing, electrodes and other device features along the same plane.

In one aspect, the present disclosure is directed to a microfluidic device comprising: a base layer, wherein the base layer comprises an encapsulated fluidic tubing, at least one encapsulated electrode, and at least one encapsulated lead, wherein an opening defining an inside diameter of the encapsulated fluidic tubing and the at least one encapsulated electrode are substantially coplanar; and a microchannel-forming layer, wherein the microchannel-forming layer comprises at least one microchannel and at least one reservoir; wherein the encapsulated fluidic tubing, the at least one encapsulated electrode, the at least one microchannel and the at least one reservoir are in fluid connection; and wherein the opening defining an inside diameter of the encapsulated fluidic tubing forms a reduced dead volume interconnect with the at least one microchannel.

In another aspect, the present disclosure is directed to a microfluidic device comprising: a base layer, wherein the base layer comprises an encapsulated fluidic tubing, at least one encapsulated electrode, at least one encapsulated lead and an integrated capillary loop, wherein an opening defining an inside diameter of the encapsulated fluidic tubing, the at least one encapsulated electrode, a first opening defining an inside diameter of the integrated capillary loop and a second opening defining an inside diameter of the integrated capillary loop are substantially coplanar; and a microchannel-forming layer, wherein the microchannel-forming layer comprises at least one microchannel and at least one reservoir; and wherein the encapsulated fluidic tubing, the at least one encapsulated electrode, the at least one microchannel, the integrated capillary loop, and the at least one reservoir are in fluid connection; and wherein the opening defining an inside diameter of the encapsulated fluidic tubing forms a reduced dead volume interconnect with the at least one microchannel.

In another aspect, the present disclosure is directed to a method for preparing a base layer of a microfluidic device, the method comprising: inserting a portion of a fluidic tubing through at least one aperture comprised in a mold, the mold defining an interior volume of the mold; inserting a portion of at least one lead connected to at least one electrode through the at least one aperture in the mold; adding a quantity of an encapsulant material to the mold, wherein the encapsulant material is uncured and wherein at least one end of the portion of the fluidic tubing extends beyond the uncured encapsulant material; curing the encapsulant material to result in a base layer of a microfluidic device, wherein the base layer comprises an encapsulated fluidic tubing, at least one encapsulated electrode and at least one encapsulated lead; removing the at least one end of the portion of the fluidic tubing that extends beyond a surface of the base layer such that an opening defining an inside diameter of the fluidic tubing is substantially coplanar with the surface of the base layer and wherein at least one end of the at least one electrode is aligned substantially coplanar with the opening defining an inside diameter of the fluidic tubing.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 6A is a graph illustrating on-capillary injection analysis using a microfluidic device of the present disclosure with an encapsulated capillary using catechol (40 nL), as described in Example 3.

FIG. 6B is a graph illustrating on-capillary injection analysis using a microfluidic device with an inserted capillary using catechol (40 nL), as described in Example 3.

FIG. 6C is a graph illustrating off-chip injection using a microfluidic device of the present disclosure with an encapsulated capillary using catechol (200 nL), as described in Example 3.

FIG. 6D is a graph illustrating off-chip injection using a microfluidic device with an inserted capillary using catechol (200 nL), as described in Example 3.

FIG. 14A is a graph showing injections of 1 μM ornithine (m/z=133) at a flow rate of 1 μL/min with a six-port injector and a 27 nL sample loop into the on-chip ESI device, as described in Example 8.

Figure 1A:
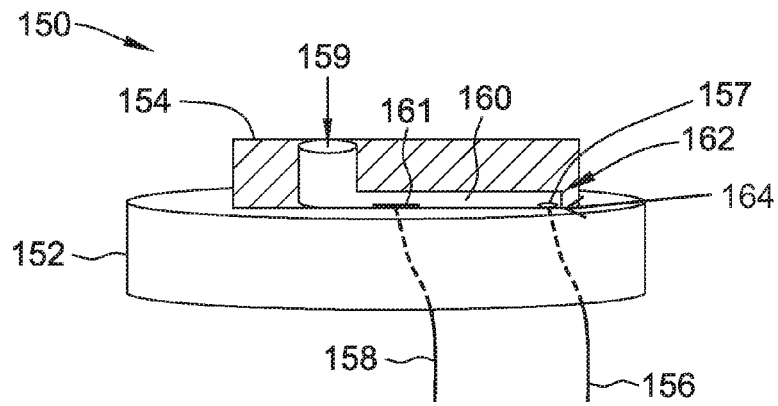
FIG. 1A is a translucent schematic illustration of an assembled microfluidic device of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

In accordance with the present disclosure, microfluidic devices and methods for assembling microfluidic devices with low dead volume interconnects are described. The devices and methods allow for encapsulating fluidic tubing and electrodes during fabrication of the microfluidic devices such that dead volume is reduced or eliminated. The microfluidic devices and methods described herein advantageously allow for the fixed alignment between the fluid interconnects and electrodes. The microfluidic devices and methods described herein also advantageously allow for housing fluidic tubing and electrodes in a rigid base layer that results in extremely robust devices.

Microfluidic Devices

In one aspect, the present disclosure is directed to a microfluidic device comprising: a base layer, wherein the base layer comprises an encapsulated fluidic tubing, at least one encapsulated electrode, and at least one encapsulated lead, wherein an opening defining an inside diameter of the encapsulated fluidic tubing and the at least one encapsulated electrode are substantially coplanar; and a microchannel-forming layer, wherein the microchannel-forming layer comprises at least one microchannel and at least one reservoir; wherein the encapsulated fluidic tubing, the at least one encapsulated electrode, the at least one microchannel and the at least one reservoir are in fluid connection; and wherein the opening defining an inside diameter of the encapsulated fluidic tubing forms a reduced dead volume interconnect with the at least one microchannel.

Microfluidic devices 150 include a rigid base layer 152 and a microchannel-forming layer 154. The base layer 152 houses at least a portion of fluidic tubing 156, an electrode 161 and at least a portion of a lead to the at least one electrode 158. An opening defining an inside diameter 157 of the encapsulated fluidic tubing 156 and the electrode 161 are substantially coplanar. As used herein, "substantially coplanar" refers to the opening defining an inside diameter 157 of the encapsulated fluidic tubing 156 and the encapsulated electrode 161 lie in the same plane such that no portion or a very small portion of the fluidic tubing 156 protrudes or extends above the top surface 153 of (or outside) the base layer 152 and/or no portion or a very small portion of the electrode 161 protrudes or extends above the top surface 153 of (or outside) the base layer 152. For example, the opening defining an inside diameter 157 of the encapsulated fluidic tubing 156 and the encapsulated electrode 161 can each terminate at the top surface 153 of the base layer 152 such that the opening defining an inside diameter 157 of the encapsulated fluidic tubing 156 and the electrode 161 are located at the top surface 153 of the base layer 152 such that no portion or a very small portion of the fluidic tubing 156 protrudes or extends above the top surface 153 of (or outside) the base layer 152 and/or no portion or a very small portion of the electrode 161 protrudes or extends above the top surface 153 of (or outside) the base layer 152. As used herein, the "top surface" 153 of the base layer 152 refers to the surface of the base layer 152 that is contacted with the microchannel-forming layer 154 of the microfluidic device 150. As further described herein, during fabrication of the base layer 152, a portion of the fluidic tubing 156 and/or the electrode can protrude or extend above the top surface 153 of the base layer 152 which can be removed after the encapsulant material is cured. Removing the portion of the fluidic tubing 156 and/or the electrode 161 that protrudes or extends above the top surface 153 of the base layer 152 can result in the opening defining the inside diameter 157 of the fluidic tubing 158 to be substantially coplanar with the top surface 153 of the base layer 152 and/or substantially coplanar with at least a portion of the electrode 158.

At least a portion of the fluidic tubing 156 and at least a portion of the at least one electrode 161 are encapsulated in the base layer 152. As illustrated in FIGS. 1B and 1C, the opening defining an inside diameter 157 of the fluidic tubing 156 and the electrode 161 can have a fixed alignment. The base layer 152 encapsulates one end of the fluidic tubing 156 such that the opening defining an inside diameter 157 of the fluidic tubing 156 is substantially coplanar with a top surface 153 of the base layer 152. The fluid interconnect 164 of the opening defining an inside diameter 157 of the fluidic tubing 156 has low to no dead volume because little to no fluidic tubing 156 protrudes or extends into the microchannel 160 of the microchannel-forming layer 154. As used herein, "fluid interconnect" refers to the connection at which the fluidic tubing inserts into the microchannel 160 of the microchannel-forming layer 154. As used herein, the phrase "dead volume" refers to a volume of fluid that results from a fluidic connection. Any fluidic connection leads to some dead volume or a volume that is additional to the microchannel volume. This volume acts as a mixing chamber and results in dilution of the fluid. This extra-column source of volume can lead to a degradation of analytical device performance including, for example, a decrease in the detector response, an increase in the device's rise time/temporal resolution, a decrease in the device's sensitivity, degradation of the device's limit of detection, an increase in peak width, and an increased dilution. As used herein "reduced dead volume" and "low dead volume" are used interchangeably herein to refer to a dead volume of 1.5 µL or less.

The base layer 152 also encapsulates at least one electrode 161 that is also substantially coplanar with the top surface 153 of the base layer 152. The at least one electrode 161 is also substantially coplanar with the opening defining the inside diameter 157 of the fluidic tubing 156. A lead 158 is coupled to the electrode 161, which is then connected to a power source (not shown). As described further herein, the electrode 161 is connected to the lead 158 prior to curing of the base layer 152 during fabrication. The lead 158 and electrode 161 can be coupled using methods known to those skilled in the art such as, for example, soldering and using an adhesive. During fabrication of the microfluidic devices of the present disclosure, at least a portion of the lead is encapsulated in the base layer. Encapsulation of the electrode coupled to the lead provides the advantage that the connection between the electrode and the lead is stabilized by the base layer.

The base layer 152 can further include a second fluidic tubing (see for example, FIG. 12). As with the fluidic tubing 156, at least a portion of the second fluidic tubing can be encapsulated by the base layer 156. The second fluidic tubing can be coupled to analytical devices such as, for example, a mass spectrometer, to integrate the microfluidic devices of the present disclosure with the analytical devices.

The microfluidic devices 150 also include a microchannel-forming layer 154. The microchannel-forming layer 154 includes at least one microchannel 160. The microchannel 160 can further include an input end 162 and a waste reservoir 159.

In the assembled configuration of the microfluidic device 150, the microchannel-forming layer 154 is placed such that the bottom surface 155 of the microchannel-forming layer 154 contacts the top surface 153 of the base layer 152. The microchannel-forming layer 154 can be reversibly sealed or irreversibly sealed with the base layer 152. The microchannel 160 of the microchannel-forming layer 154 is positioned such that it overlays the electrode 161 and the input end 162 of the microchannel 160 is placed proximate to the opening defining an inside diameter 157 of the fluidic tubing 156. The microchannel-forming layer 154 defines a portion of a fluidic channel 160. The fluidic microchannel 160, in some examples, is defined in a bottom surface 155 of the microchannel-forming layer 154 such that the microchannel 160 is not completely encapsulated within the microchannel-forming layer 154. Further, during assembly, the microchannel-forming layer 154 is aligned relative to the base layer 152 such that the microchannel 160 extends across the opening defining an inside diameter 157 of the fluidic tubing 156 and the at least one electrode 161. In some embodiments, the opening defining an inside diameter 157 of the fluidic tubing 156 can be aligned at one end of the microchannel 160 defining a fluidic interconnect 164 (i.e., the area near where the microchannel 160 communicatively couples with the opening defining an inside diameter 157 of the fluidic tubing 156). Advantageously, microfluidic devices with base layers having encapsulated fluidic tubing, encapsulated electrodes and encapsulated leads allows for aligning electrodes and fluidic tubing in the same plane (i.e., substantially coplanar) so that with polishing the opening defining an inside diameter 157 of the fluidic tubing 156 is flush with the top surface 153 of the base layer 152. It is not feasible to ensure this flushness with the inserted method in which fluidic tubing (e.g., fluidic tubing 256 illustrated in FIG. 2A) is inserted through the microchannel-forming layer (e.g., microchannel-forming layer 256 illustrated in FIG. 2A).

Alignment of the electrode 161 and the opening defining the inside diameter 157 of the fluidic tubing 156 also provides ease of use for less experienced users. For example, alignment of the electrode 161 and the opening defining the inside diameter 157 of the fluidic tubing 156 provides landmark points for assembly of the base layer 152 with the microchannel-forming layer 154 such that the user can properly overlay the microchannel 160 of the microchannel-forming layer 154 such that the microchannel 160 passes over the electrode 161 and the opening defining the inside diameter 157 of the fluidic tubing 156.

During operation, fluid passes through the fluidic tubing 156, through the opening defining the inside diameter 157 of the fluidic tubing 156, and into microchannel 160 at the fluidic interconnect 162. The fluid then passes through microchannel 160 and over the at least one electrode 161, which perform various operations on the fluid as described herein, and collects in a waste reservoir 159. Because the opening defining the inside diameter 157 of the fluidic tubing 156 is substantially coplanar with the top surface 153 of the base layer 152, the fluidic interconnect 162 forms a low to no dead volume fluid interconnect. Further, because at least a portion of the fluidic tubing 156, including the opening defining the inside diameter 157, is encapsulated in, and thus fixedly coupled to, the hardened base layer 152, the microfluidic device 150 has additional rigidity and stability.

Figure 1B:
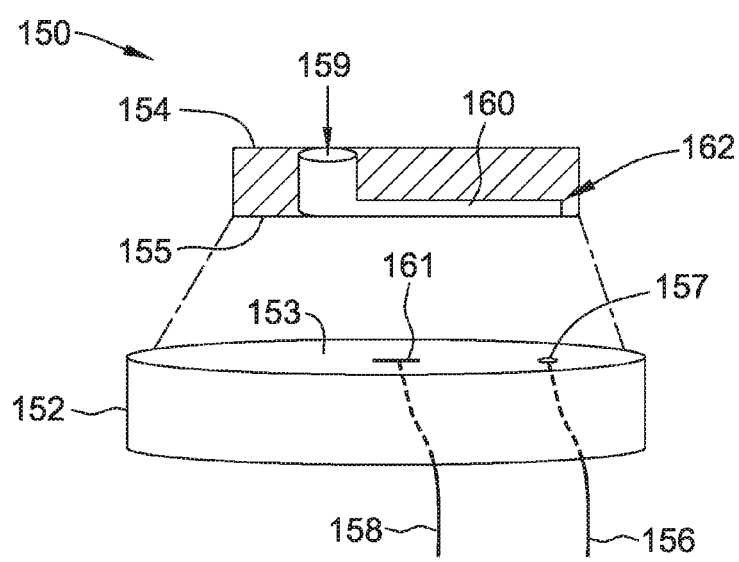
FIG. 1B is an exploded view of the translucent schematic illustration of the microfluidic device shown in FIG. 1A.
Figure 1C:
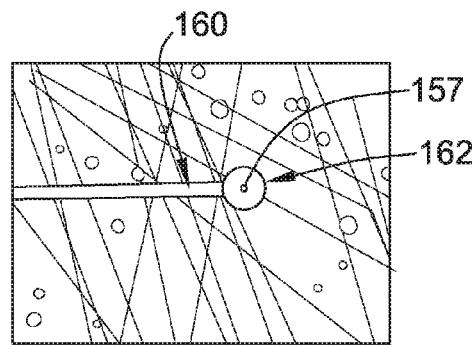
FIG. 1C is a schematic illustration of a top view of the interface between the tubing outlet and a microchannel of a microchip.
Figure 1D:
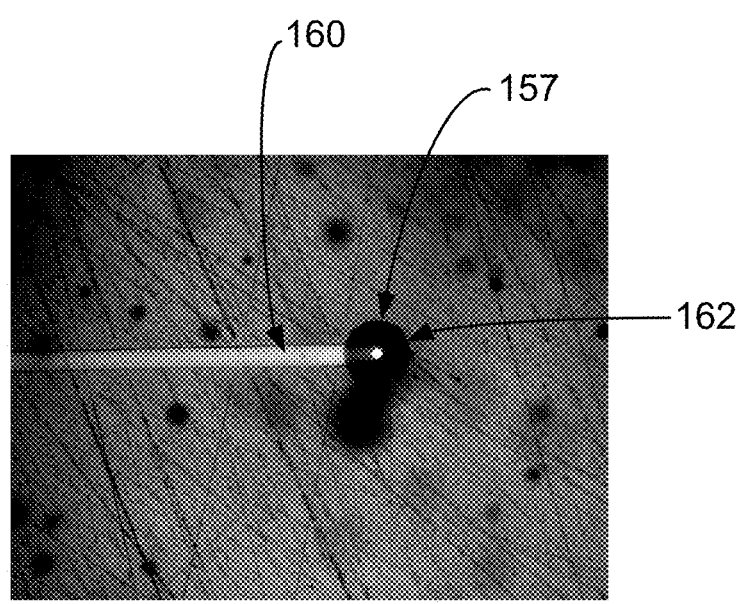
FIG. 1D is a photograph showing a top view of the interface between the tubing outlet and a microchannel of a microchip.

FIG. 1C is an image showing a vertical aspect view of the exemplary fluidic interface between the opening defining an inside diameter 157 of the fluidic tubing (e.g., fluidic tubing 156 as shown in FIGS. 1A and 1B) and the microchannel 160 of the microchannel-forming layer (e.g., microchannel-forming layer 154, as shown in FIG. 1A). FIG. 1D is a photographic image of the same exemplary fluidic interface illustrated in FIG. 1C.

Figure 2A:
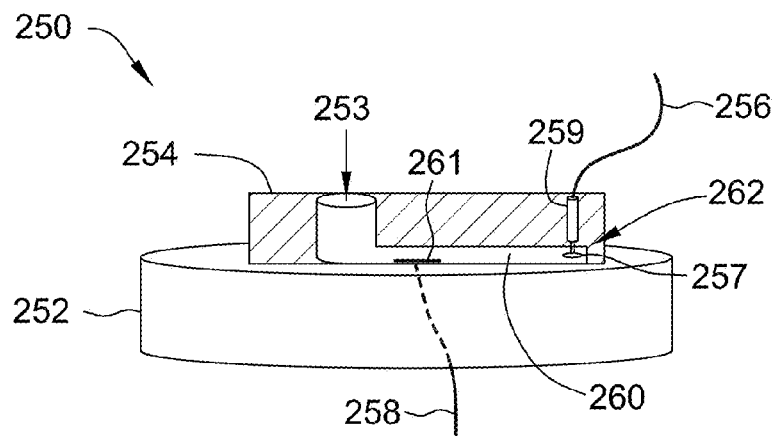
FIG. 2A is a translucent schematic illustration of a microfluidic device fabricated by inserting tubing according to the prior art method.
Figure 2B:
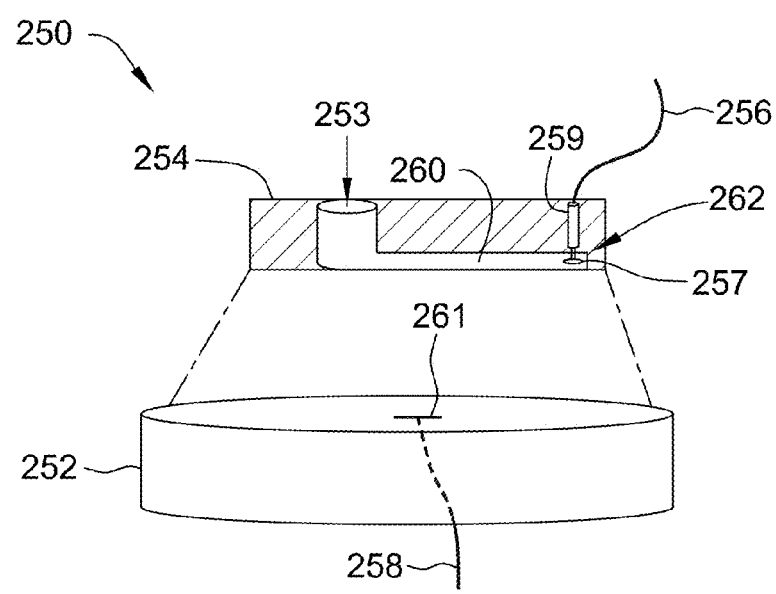
FIG. 2B is an exploded view of the translucent schematic illustration of the microfluidic device shown in FIG. 2A.

For comparison, FIGS. 2A and 2B illustrate an example microfluidic device 250 assembled using the prior art method of inserting the tubing 256 through the microchannel-forming layer 254. This microfluidic device includes a base layer 252 coupled with a microchannel-forming layer 254. An opening defining the inside diameter 257 of the fluidic tubing 256 defines a tubing outlet. The base layer 252 includes an electrode 261 coupled with a lead 258. The microchannel-forming layer 254 includes a fluidic microchannel 260 similar to a microfluidic device 150 of the present disclosure shown in FIG. 1. The microchannel-forming layer 254, in some examples, is formed from soft materials, such as PDMS. Because the microfluidic device 250 is prepared by inserting the fluidic tubing 256 through the microchannel-forming layer 254, this microchannel-forming layer 254 includes a tubing microchannel 259 to provide a stable connection between the fluidic tubing 256 and the microchannel-forming layer 254. Unlike microfluidic devices of the present disclosure that have base layers with encapsulated fluidic tubing and electrodes that are flush with the top surface of the base layer, it is not feasible to ensure this flushness with devices fabricated by inserting the fluidic tubing through the microchannel-forming layer. Additionally, the fluid interconnect 262 between the opening defining the inside diameter 257 of the fluidic tubing 256 and the tubing microchannel 259 is less stable than the microfluidic devices of the present disclosure, which can lead to higher dead volume as the fluidic tubing 256 and/or the tubing microchannel 259 protrudes or extends into the microchannel 260.

During assembly, one end of the fluidic tubing 256 is extended through the tubing channel 259 such that the opening defining the inside diameter 257 of the fluidic tubing 256 is disposed a distance into the microchannel 260. As such, a fluidic interconnect 262 between the tubing 256 and the microchannel 260 consumes some volume ("dead volume") of the microchannel 260 (i.e., the volume occupied by the tip of the fluidic tubing 256 and/or tubing microchannel 259 that extends into the microchannel 260). The fluidic tubing 256 is not fixedly coupled to the microchannel-forming layer 250 (i.e., it is merely pushed through the tubing channel 259). Thus, any perturbation of the fluidic tubing 256 relative to the entire microfluidic device 250 may cause the fluidic tubing 256, the opening defining the inside diameter 257, and/or the tubing channel 259 to shift or change positions within the microfluidic device 250, which can have undesirable effects on properties of the fluid flow and lead to an increase in dead volume.

During operation, fluid passes through the tubing 256 and into the microchannel 260 at the tubing channel 259. The fluid then passes through microchannel 260 and over the at least one electrode 261, which perform various operations on the fluid as described herein, and collects in a waste reservoir 253.

In another aspect, the present disclosure is directed to a microfluidic device comprising: a base layer, wherein the base layer comprises an encapsulated fluidic tubing, at least one encapsulated electrode, at least one encapsulated lead and an integrated capillary loop, wherein an opening defining an inside diameter of the encapsulated fluidic tubing, the at least one encapsulated electrode, a first opening defining an inside diameter of the integrated capillary loop and a second opening defining an inside diameter of the integrated capillary loop are substantially coplanar; and a microchannel-forming layer, wherein the microchannel-forming layer comprises at least one microchannel and at least one reservoir; and wherein the encapsulated fluidic tubing, the at least one encapsulated electrode, the at least one microchannel, the integrated capillary loop, and the at least one reservoir are in fluid connection; and wherein the opening defining an inside diameter of the encapsulated fluidic tubing forms a reduced dead volume interconnect with the at least one microchannel.

Figure 3A:
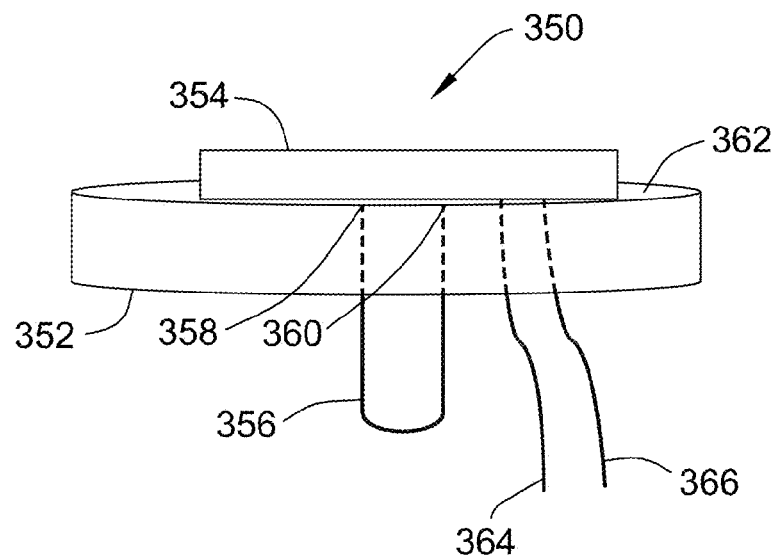
FIG. 3A is a translucent schematic illustration of an assembled microfluidic device of the present disclosure having a capillary loop.

As described above, the microfluidic device includes a base layer and a microchannel-forming layer. An exemplary microfluidic device of this embodiment further includes a capillary loop. As illustrated in FIG. 3A, the microfluidic device 350 includes a base layer 352 and a microchannel-forming layer 354. The base layer 350 includes a capillary loop 356. As described above for the fluidic tubing, at least a portion of each end of the capillary loop 356 shown is encapsulated by the base layer 352. Further, a first opening defining an inside diameter 358 of the encapsulated capillary loop 356 and a second opening defining an inside diameter 360 of the encapsulated capillary loop 356 are encapsulated by the base layer 352 such that the first opening 358 and second opening 360 are substantially coplanar with a top surface 362 of the base layer 352. The fluid interconnects of the first opening 358 and the second opening 360 of the capillary loop 356 have low to no dead volume because little to no capillary loop 356 protrudes or extends into the microchannel (not shown in FIG. 3A) of the microchannel-forming layer 354. The base layer 352 also encapsulates at least one electrode (see e.g., FIG. 3B 378 and 380) that are also substantially coplanar with the top surface 362 of the base layer 352. As illustrated in the exemplary embodiment shown in FIG. 3A, the base layer 352 encapsulates at least a portion of a lead 364 to electrode 378 and encapsulates at least a portion of a lead 366 to electrode 380.

Figure 3B:
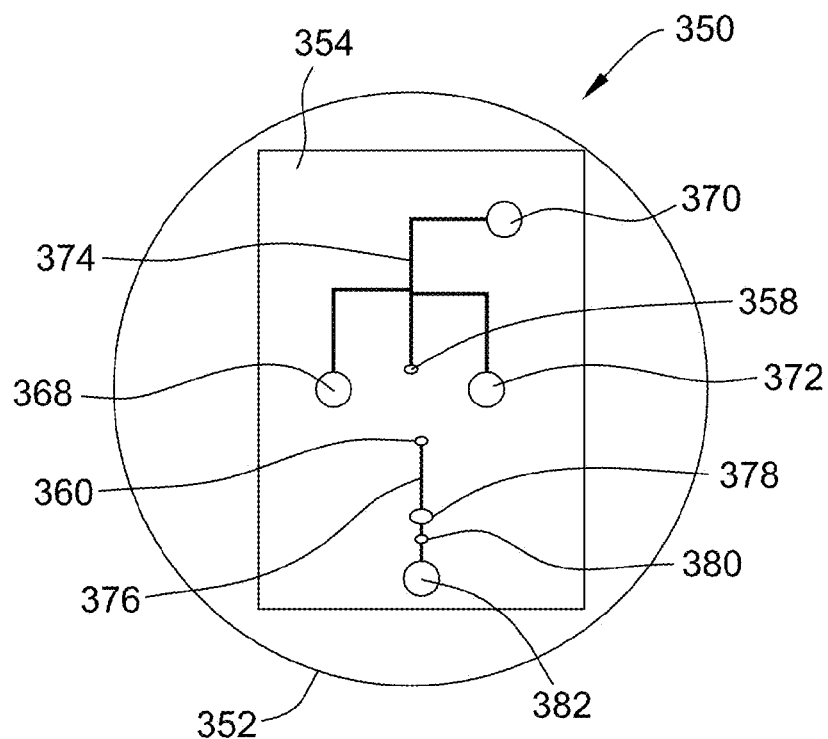
FIG. 3B is a top view schematic illustration of an assembled microfluidic device having a capillary loop of the present disclosure.

As shown in the top view illustration in FIG. 3B of the microfluidic device 350 having a capillary loop, the microchannel-forming layer 354 can include at least one reservoir such as, for example, a sample reservoir 368, a buffer reservoir 370 and a waste reservoir 372. The sample reservoir 368, the buffer reservoir 370 and the waste reservoir 372 of the microchannel-forming layer 354 are in fluid connection by at least one microchannel 374. The fluid interconnect of the first opening 358 of the capillary loop (not visible in FIG. 3B) is also in fluid connection with the sample reservoir 368, the buffer reservoir 370 and the waste reservoir 372 of the microchannel-forming layer 354 by the at least one microchannel 374. The fluid interconnect of the second opening 360 of the capillary loop (not visible in FIG. 3B) couples the capillary loop to a second microchannel 376 of the microchannel-forming layer 354.

The exemplary microfluidic device illustrated in FIGS. 3A and 3B also includes electrodes 378 (coupled to lead 364) and 380 (coupled to lead 366). As shown in FIG. 3B, the second microchannel 376 overlays electrode 378 and electrode 380. In a particularly preferred embodiment, electrode 378 functions as a decoupler (ground) electrode and electrode 380 functions as a working electrode. As described herein, electrode 378 and electrode 380 are substantially coplanar with the top surface 362 of the base layer. As also described herein, electrode 378 and electrode 380 are aligned with the second opening defining the inside diameter 360 of the capillary loop where it enters the second microchannel 376, as well as with the second microchannel 376 and an auxiliary reservoir 382. The microchannel-forming layer 354 can further include an auxiliary reservoir 382 in fluid communication with the second opening 360 of the capillary loop (not visible in FIG. 3B) via the second microchannel 376. The auxiliary reservoir 382 can be coupled with additional electrodes (not shown) such as, for example a counter electrode, a reference electrode, an auxiliary electrode and combinations thereof.

The integrated capillary loop can be made using any tubing known to those skilled in the art and as described herein. A particularly suitable capillary loop tubing material for electrophoretic separations can be, for example, fused-silica.

The length of the capillary loop and the microchannels define the separation length of the integrated capillary loop. As used herein, "separation length" refers to the total length of the capillary loop and the microchannels as measured from the intersection of the microchannels from each reservoir (see, e.g., FIG. 3B the "+" intersection between the microchannels leading from the buffer reservoir 370, the sample reservoir 368 and the waste reservoir 372), the capillary loop length and the microchannel terminating at the auxiliary reservoir 382. Advantageously, the separation length improves the resolution capabilities of microchip electrophoresis. The capillary loop can have a length of from about 5 cm to about 100 cm. Particularly suitable capillary loop separation length can be from about 5 cm to about 20 cm.

The inside diameter (i.d.) of the integrated capillary loop can be of any inside diameter known to those skilled in the art. Particularly suitable inside diameter of the integrated capillary loop can be, for example, 25 µm i.d. to about 100 µm i.d., including, for example, 50 µm i.d. to 75 µm i.d.

As illustrated in FIG. 3A, the capillary loop 356 is integrated into the base layer 352 in a manner similar to how the base layer 152 houses at least a portion of fluidic tubing 156, the at least one electrode 156 and at least a portion of lead 364 and lead 366 as described herein. In particular, the base layer 352 of the microfluidic device 350 having the integrated capillary loop 356 can be fabricated using any encapsulant material that will harden upon curing as described herein.

The base layer 352 also encapsulates at least one electrode 378 and 380 that are also coplanar with the top surface 362 of the base layer 352. The at least one electrode can be, for example, a decoupler electrode (see, FIG. 3B electrode 378), a working electrode (see, FIG. 3B electrode 380) and combinations thereof.

The decoupler and working electrodes can be made of any suitable material known by those skilled in the art. Particularly suitable electrode materials can be, for example, palladium, platinum, gold, mercury-modified gold, glassy carbon, carbon fiber, nickel, mercury-modified platinum, mercury-modified palladium, carbon paste, silver, copper, graphite, titanium, chromium, mixed metal oxides, and carbon nanotube-containing electrodes.

A particularly suitable decoupler material can be, for example, palladium. The decoupler electrode functions as a ground.

A particularly suitable working electrode material can be, for example, platinum. The working electrode functions as a detection electrode.

The base layers of the microfluidic devices of the present disclosure can be fabricated using any encapsulant material that will harden upon curing. Particularly suitable materials are materials that are transparent or translucent upon curing. Other particularly suitable materials include those that are non-toxic to cells. The base layer can be fabricated using materials such as, for example, epoxy, polystyrene, polycarbonate, polyester, polymethylmethacrylate, thermoset polyester, polyurethane-methacrylate cyclic olefin copolymer, polyvinylchloride, and polyethyleneterephthalate glycol, polyethyleneterephthalate and combinations thereof. Particularly suitable materials are transparent or translucent, and non-toxic to cells upon curing such as, for example, polystyrene, polycarbonate, polyester, polymethylmethacrylate, thermoset polyester, polyurethane-methacrylate cyclic olefin copolymer, polyvinylchloride, polyethyleneterephthalate glycol, polyethyleneterephthalate and combinations thereof.

The fluidic tubing and capillary loop of the present disclosure can be made of any suitable material known by those skilled in the art. Particularly suitable fluidic tubing and capillary loop materials can be, for example, a fused silica capillary, a polyetheretherketone (PEEK) tubing, a perfluoroalkoxy (PFA) tubing, a fluorinated ethylene propylene (FEP) tubing, a stainless steel tubing, a Halar (ethylene-chlorotrifluoroethylene) tubing, a tygon tubing, a thermoplastic elastometer polypropylene tubing (e.g., PHARMED® ISMAPRENE tubing; PHARMED® BPT tubing), a polyphenylsulfone tubing, an ethylene-tetrafluoroethylene tubing and combinations thereof.

The electrodes of the present disclosure can be made of any suitable material known by those skilled in the art. Particularly suitable electrode materials can be, for example, palladium, platinum, gold, mercury-modified gold, glassy carbon, carbon fiber, nickel, mercury-modified platinum, mercury-modified palladium, carbon paste, silver, copper, graphite, titanium, chromium, mixed metal oxides, carbon nanotube-containing materials and combinations thereof. Particularly suitable electrodes can be, for example, a palladium electrode, a platinum electrode, a gold electrode, a mercury-modified gold electrode, a glassy carbon electrode, and a carbon fiber electrode, a nickel electrode, a mercury-modified platinum electrode, a mercury-modified palladium electrode, a carbon paste electrode, a silver electrode, a copper electrode, a graphite electrode, a titanium electrode, a chromium electrode, a mixed metal oxide electrodes, a carbon nanotube-containing electrode, an Indium tin oxide electrode and combinations thereof.

The microchannel-forming layers of the present disclosure can be made of any suitable material known by those skilled in the art. Suitable materials can be, for example, a silicon-based organic polymer. A particularly suitable material can be polydimethylsiloxane (PDMS). Other suitable materials for fabricating the microchannel-forming layer can be, for example, materials that can be bonded to the base layer such as, for example, epoxy, polystyrene, polycarbonate, polyester, polymethylmethacrylate, thermoset polyester, polyurethane-methacrylate cyclic olefin copolymer, polyvinylchloride, polyethyleneterephthalate glycol, polyethyleneterephthalate and combinations thereof.

The microfluidic devices of the instant application can further be connected to a voltage supply as known to those skilled in the art.

The applicability of the microfluidic devices of the present disclosure having encapsulated fluidic tubing enables integrating several off-chip analytical methods to the microfluidic device. This includes droplet transfer, droplet desegmentation, microchip-based flow injection analysis, and microdialysis sampling. The microfluidic devices of the present disclosure advantageously improve analytical performance when compared to microfluidic devices having fluidic interconnects with an appreciable dead volume that results from the portion of fluidic tubing that protrudes or extends into the microchannel. Further, application of the microfluidic devices of the present disclosure can be extended to couple conventional CE with electrochemical detection because of the encapsulated tubing and encapsulated grounding electrodes, such as palladium electrodes, and detector electrodes, such as platinum electrodes.

Methods of Fabricating Microfluidic Devices

In another aspect, the present disclosure is directed to methods of fabricating microfluidic devices. The method includes: inserting a portion of a fluidic tubing through at least one aperture comprised in a mold, the mold defining an interior volume of the mold; inserting a portion of at least one lead connected to at least one electrode through the at least one aperture in the mold; adding a quantity of an encapsulant material to the mold, wherein the encapsulant material is uncured and wherein at least one end of the portion of the fluidic tubing extends beyond the uncured encapsulant material; curing the encapsulant material to result in a base layer of a microfluidic device, wherein the base layer comprises an encapsulated fluidic tubing, at least one encapsulated electrode and at least one encapsulated lead; removing the at least one end of the portion of the fluidic tubing that extends beyond a surface of the base layer such that an opening defining an inside diameter of the fluidic tubing is substantially coplanar with the surface of the base layer and wherein at least one end of the at least one electrode is aligned substantially coplanar with the opening defining an inside diameter of the fluidic tubing. The method can further include coupling the base layer with a microchannel-forming layer. When the base layer is coupled with a microchannel-forming layer, the device presents a low dead volume fluidic interconnect between the fluidic tubing and a microchannel of the microchannel-forming layer.

The method can further include inserting at least one portion of a capillary loop through at least one aperture included in the mold. For example, a portion of the capillary loop (such as capillary loop 356 show in FIG. 3A) having the first opening (such as opening 358) can be inserted through an aperture in the mold. Additionally, the method can include inserting a portion of the capillary loop (such as capillary loop 356 show in FIG. 3A) having the second opening (such as opening 369) can be inserted through an aperture in the mold.

The method can further include coupling the at least one electrode to a lead. The at least one electrode coupled to the lead can then be inserted through at least one aperture included in the mold. Upon curing of the encapsulant material, at least a portion of the electrode and at least a portion of the lead are encapsulated in the base layer.

The mold can include as many apertures as desired for inserting fluidic tubing, electrodes, leads, capillary loops and other device features. The mold can include a separate aperture for each device feature to be encapsulated such that each device feature can be inserted through its own aperture. The mold can also include apertures sized such that a single device feature can be inserted through the aperture. The mold can also include aperture sizes such that more than one device feature can be inserted through the same aperture. The mold can include, for example, at least one aperture. The mold can also include, for example, at least two apertures. The mold can also include, for example, at least three apertures. The mold can also include, for example, at least four apertures. The mold can also include, for example, at least five apertures. The mold can also include, for example, six apertures. The mold can also include, for example, at least seven apertures. The mold can also include, for example, at least eight apertures. The mold can also include, for example, at least nine apertures. The mold can also include, for example, at least ten apertures. The mold can also include, for example, more than ten apertures.

Further, the microfluidic devices can be integrated with additional analytical methods through low dead volume fluidic interconnects. For example, the microfluidic devices of the present disclosure can be integrated with capillary electrophoresis, electrochemical detection, droplet transfer, droplet desegmentation and microchip-based flow injection, electrospray ionization, mass spectrometry, cell culture and combinations thereof.

The microchannel-forming layer can, for example, be manufactured using photolithography. Photolithography includes the fabrication of negative masters using materials such as, for example SU-8 10 photoresist and SU-8 50 photoresist. Upon curing, the microchannel-layer is peeled from the master and contacted with the base layer as described herein. The microchannel-forming layer can also be manufactured, for example, by embossing, injection molding, etching, or dissolving microchannels in the substrate materials.

The mold can be any suitable container that can hold a volume of encapsulant. The mold can be, for example, a Teflon mold, a weigh boat, or a disposable aluminum dish. The mold defines an interior portion into which encapsulant is inserted, as described below. An aperture is formed through a surface of the mold. One end of fluidic tubing and/or capillary loop is extended through the aperture. The fluidic tubing and/or capillary loop can have an outer diameter approximately equal to a diameter of the aperture. In some embodiments, a fluidic tubing and/or a capillary loop outlet is disposed on the interior side of the mold. In other embodiments, a fluidic tubing and/or a capillary loop outlet is disposed on the exterior side of the mold. These two alternate configurations suggest which side of the resulting base layer will be used as the top surface of the base layer that will interface with the microchannel-forming layer.

Further, at least one electrode is placed in the mold. Suitable material for forming the electrodes are described herein. The electrode is positioned such that it will be substantially coplanar with the top surface (for example, top surface 153) of the base layer (for example, base layer 152). As such, in some examples, at least a portion of the electrode material is placed along the bottom interior surface of the mold itself, prior to adding the encapsulant material to the mold. In this embodiment, the base of the encapsulant material contained in the mold (i.e., the bottom of the volume adjacent to the body of the mold itself) will form the top surface (for example, top surface 153) of the base layer that interfaces with the microchannel-forming layer (for example, microchannel-forming layer 154). Alternatively, the electrodes can be placed on top of the encapsulant material after the encapsulant material is added to the mold. In this embodiment, the surface of the encapsulant material forms the top surface (for example, top surface 153) that interfaces with the microchannel-forming layer (for example, microchannel-forming layer 154). The electrodes can also include leads that may also be extended through the encapsulant in similar fashion as described for inserting the fluidic tubing into the mold. In a particularly preferred method, the electrode is coupled with the lead prior to placing the electrode and/or lead in the mold or encapsulant material. The electrode is coupled with the lead using methods known to those skilled in the art such as, for example, soldering and with adhesives. Once the electrode and lead are coupled, the electrode can be inserted through an aperture of the mold such that a portion of the lead remains in the mold and a portion of the lead passes through the aperture and out of the mold. As described herein, encapsulant material that is uncured is then added to the mold such that it surrounds the portion of the lead contained within the mold and such that the electrode is positioned at the top surface or just below the top surface of the electrode. Upon curing of the encapsulant material, the cured encapsulant material surrounds the portion of the lead in the mold. The cured encapsulant also surrounds the connection between the electrode and the lead such that the connection is contained within the stable, rigid base layer to protect and stabilize the connection between the electrode and the lead. The cured encapsulant material also partially or completely surrounds the electrode. At least a portion of the electrode surface can be exposed by polishing the top surface of the base layer as described herein.

An amount of encapsulant material is then added into the interior volume of the mold. Suitable encapsulant materials are described herein. If the opening of the fluidic tubing and/or the first opening of the capillary loop and/or the second opening of the capillary loop is disposed on the interior side of the mold (i.e., a configuration such that the surface of the encapsulant material added to the mold will be the top surface (for example, top surface 153) that interfaces with the microchannel-forming layer (for example, microchannel-forming layer 154), then the encapsulant material is added to the interior volume of the mold such that it does not rise to a level above the fluidic tubing and/or capillary loop openings (i.e., there will be a portion of the fluidic tubing and/or capillary loop, including the opening, that remains exposed).

The encapsulant material is then allowed to cure. As used herein, "cure" is used according to its ordinary meaning as understood by one skilled in the art to refer to hardening of the encapsulant material. In some embodiments, the encapsulant is epoxy, and is allowed to cure at room temperature for about 2 hours. In other embodiments, the encapsulant is polystyrene. For polystyrene-devices, polystyrene powder is poured into the mold and heated at a suitable temperature and length of time to melt the polystyrene powder. A particularly suitable temperature is about 250° C. A particularly suitable length of time is about 2 hours. The mold can be covered for a more uniform heating until the powder is melted. Additional polystyrene powder can be added as needed throughout the heating process. The resulting base layer is then allowed to cool to room temperature.

After curing, the surface of the resulting base layer may have an exposed section of fluidic tubing (for example, fluidic tubing 156) or capillary loop (for example, capillary loop 356). The exposed section of fluidic tubing or capillary loop can be removed such that the fluidic tubing opening (for example, opening 157 of the fluidic tubing outlet 157), the first opening and the second opening of the capillary loop (for example, first opening 358 and second opening 360 of capillary loop 356) is substantially coplanar with the top surface. The base layer may also be polished along the top surface. In some embodiments, the top surface is wet polished using a range of grits 200-1200 (such as those commercially available from Buehler, Lake Bluff, Ill.) to achieve a smooth surface for incorporation with microchips. Polishing can be achieved using methods known by those skilled in the art such as, for example, polishing using a variable speed grinder-polisher (such as those commercially available from Buehler, Lake Bluff, Ill.). Further, if the fluidic tubing and/or capillary loop clogs during polishing or other steps of the method, the base layer can be treated to dislodge any material from the fluidic tubing and/or capillary loop. A particularly suitable method for dislodging material can be, for example, sonication in water about 10 minutes.

After curing, the method can further include coupling a microchannel-forming layer with the base layer as described herein.

The resulting polished base layers results in a smooth surface that can be sealed against a microchannel-forming layer to form the microchannel-forming layer-base layer interface. The resulting base layer is rugged, with the fluid tubing, the capillary loop (in embodiments having a capillary loop) and electrode alignment being fixed so that the microchannel-forming layer can be reversibly sealed with the base layer for integrated detection. In some embodiments, the microfluidic devices can be disassembled, polished as desired (to create a fresh electrode surface), and reassembled. Additionally, if desired, the microchannel-forming layer can be fabricated with the same material as the base layer. Microchannels can be made in a microchannel-forming layer formed using the same encapsulant material used to form the base layer by embossing, injection molding, etching, or dissolving the encapsulant material. The microchannel-forming layer and base layers made using the same encapsulant material can be bonded together by bringing them into close contact and heating around the glass transition temperature (Tg) of the encapsulant materials.

Other electrodes such as, for example, counter electrodes, reference electrodes, auxiliary electrodes and combinations thereof can be prepared as described herein. The other electrodes can be coupled to leads as described herein and can be inserted through the microchannel-forming layer such that these other electrodes and their leads are encapsulated by the base layer. The other electrodes can be coupled to leads as described herein and can be encapsulated by the base layer as described herein. The counter electrode and other electrodes can be made using the electrode materials described herein.

The microfluidic devices of the instant application can further be connected to a voltage supply as known to those skilled in the art.

EXAMPLES

It is shown, in the examples below, that a variety of fluidic tubing can be encapsulated with the methods described herein, with the resulting fluidic tubing-microchannel-forming layer interface not leading to significant band broadening or plug dilution. The applicability of the microfluidic devices with encapsulated fluidic tubing was demonstrated by integrating several off-chip analytical methods to the microfluidic devices. These include droplet transfer, droplet desegmentation, and microchip-based flow injection analysis. Off-chip generated droplets may be transferred to the microfluidic devices with minimal coalescence, while flow injection studies showed improved peak shape and sensitivity when compared to the use of fluidic interconnects in prior art devices having an appreciable dead volume. In some examples, a low dead volume approach may be extended to also enable the integration of conventional capillary electrophoresis (CE) with electrochemical detection. Fused silica capillary was encapsulated, along with palladium (for grounding the electrophoresis voltage) and platinum (for detection) electrodes. As such, up to 128,000 theoretical plates for dopamine is possible. The fluidic tubing and electrodes are housed in a rigid base, enabling robust microfluidic devices that will be of interest to those skilled in the art wanting to develop microchips for use by non-experts.

Microchannel-Forming Layer

Microchannel-layers were prepared from PDMS (polydimethylsiloxane) using photolithography and silicon masters. Negative masters were fabricated using standard SU-8 50 photoresist. The structure heights were measured with a profilometer (commercially available from Veeco Instruments, Woodbury, N.Y.). Various microchannel dimensions were utilized for integrating the different analytical methods described herein. A 20:1 PDMS:curing agent ratio was used. The microchannel dimensions for each were: the droplet transfer studies=200 μm (in width)×105 μm; the desegmentation experiments=40 μm (in width)×15 μm; and the flow analysis studies=100 μm (in width)×65 μm. For the conventional CE with electrochemical detection experiments, the microchannel used to integrate the fluidic tubing with the decoupler electrode was either 100 μm (in width)×65 μm or 75 μm (in width)×25 μm. For the inserted method, microchips contained an inlet hole that was created using a 20-gauge Luer stub adapter (Becton Dickinson, Sparks, Md.). The diameter of the inlet hole was measured by microscopy to be 830 μm. The fluidic tubing was inserted approximately half way into the inlet hole. With ~6 mm thick chips used in these studies, this led to an approximate dead volume for the inlet hole of ~1.6 μL.

Encapsulation of Fluidic Tubing and Electrodes

In the below examples, microfluidic devices were fabricated using epoxy or polystyrene. The fluidic tubing included fused silica capillary, perfluoroalkoxyalkane (PFA), fluorinated ethylene propylene (FEP), or polyetheretherketone (PEEK). Incorporating fluidic tubing into these devices involved preparing the desired type and length of fluidic tubing, a hole was punched into an aluminum weigh boat, fluidic tubing was aligned with the hole, and epoxy or polystyrene was poured into the weigh boat, which was used as a mold. The fluidic tubing was allowed to protrude past the aluminum weigh boat to avoid clogging. The epoxy devices were allowed to cure at room temperature for about 2 hours. For polystyrene-devices, polystyrene powder (250 μm particle size, commercially available from Goodfellow, Oakdale, Pa.) was poured into the aluminum weigh boat and heated at 250° C. for approximately 2 hours. The weigh boat was then covered for a more uniform heating until the powder was melted, with additional powder being added to the boat as needed throughout the heating process. The substrate was then allowed to cool to room temperature. Epoxy/polystyrene base layers were wet polished using a range of grits 200-1200 (commercially available from Buehler, Lake Bluff, Ill.) to achieve a smooth surface for incorporation with microchannel-forming layers. Polishing was achieved using a variable speed grinder-polisher (commercially available from Buehler, Lake Bluff, Ill.). If the fluidic tubing became clogged after polishing, the base layer was sonicated in water for ~10 min to dislodge any material.

In some examples, electrodes are prepared as described above. A linear alignment of the fluidic tubing i.d. and the electrode advantageously ensures proper integration with the microfluidic channels post fabrication. For the droplet transfer and desegmentation studies, 150 μm-i.d. PFA fluidic tubing was encapsulated into a polystyrene device. For the flow analysis examples described herein, an epoxy device that incorporated 50 μm-i.d. fused silica capillary and a glassy carbon detection electrode (1 mm dia.) was utilized. For conventional CE studies, an epoxy device was used with a 50 μm-i.d. fused silica capillary that was aligned with a palladium decoupler (1 mm and 2 mm diameter) and a platinum electrode (0.5 mm diameter).

Microfluidic devices with encapsulated fluidic tubing, such as device 150 as shown in FIGS. 1A and 1B, were compared with microfluidic devices fabricated by inserting the fluidic tubing directly into the PDMS microchannel-forming layer (as shown for device 250 shown in FIGS. 2A and 2B). Inserting the fluidic tubing directly into the PDMS microchannel-forming layer led to a relatively large amount of dead volume (with these devices, ~1.6 μL). The amount of dead volume with this type of connection was dependent upon how far the fluidic tubing was pressed in the device and/or the size of the connecting hole. Further, the exact dead volume of this type of interconnect varied by device. In addition, this type of inserted connection was not very stable, with any perturbation to the fluidic tubing causing leakage or causing the chip to no longer be sealed.

The encapsulation approach was used to fabricate microfluidic devices to integrate off-chip functions such as droplet transfer, droplet desegmentation, microchip-based flow analysis, and conventional CE with a microchip device. One feature of these encapsulated fluidic tubing interconnects is a low dead volume interface.

For the droplet transfer example described herein, as well as the microchip-based flow described herein, comparisons were made between microfluidic devices having base layers with encapsulated fluidic tubing and encapsulated electrodes and microfluidic devices with fluidic tubing inserted through the microchannel-forming layer. For the inserted method, the fluidic tubing was inserted approximately half-way into a PDMS microchannel-forming layer with a luer stub adapter being used to make a hole into which the fluidic tubing could be inserted.

Imaging

All images, except for desegmentation interface shown in FIGS. 4E and 4F, were obtained using a fluorescence microscope (IX71, Olympus America), equipped with a 100 W Hg arc lamp, fluorescein filters, and a cooled 12-bit monochrome Qicam Fast digital CCD camera (commercially available from QImaging, Montreal, Canada). Images were captured with Streampix Digital Video Recording software (commercially available from Media Cybernetics, Silver Spring, Md.). For studies involving measuring fluorescence intensity over time, this software allows pixel integration over a user specified area. The data was output to a Microsoft Excel file, and the resulting data was processed using ChromPerfect software (Justice Laboratories, Denville, N.J.). The images were analyzed with Q Capture Pro software (commercially available from QImaging, Montreal, Canada). The images in FIGS. 4E and 4F were captured using an upright microscope, Olympus EX 60, equipped with a Qicam Fast digital CCD camera and Streampix Digital Video Recording software.

Example 1

Flow Injection Analysis

To first investigate the amount of band broadening that arises from transferring an analyte band from tubing onto a microfluidic device having encapsulated fluidic tubing, a flow injection comparison was made with a 50 μm i.d. fluidic tubing device made with inserted fluidic tubing, such as device 250 (FIG. 2A), and a 50 μm i.d. fluidic tubing encapsulated in epoxy device, such as microfluidic device 150 illustrated in FIG. 1A. For the device, a detection window was made 25 cm from the inlet. With the encapsulated fluidic tubing device, a microchannel-forming layer was sealed over the encapsulated fluidic tubing i.d. (see FIGS. 1C and 1D for a micrograph of the fluidic tubing-microchannel interface), and detection was made in the devices after the plug had been transferred (length to the detection zone was also 25 cm). For both microfluidic devices, a 40 nL fluorescein plug was hydrodynamically injected into the fluidic tubing inlet. After injection, buffer was used to pump the plugs through the fluidic tubing at 10 psi. The amount of fluorescence was monitored as a function of time at the detection window with a fluorescence microscope.

Figure 4:
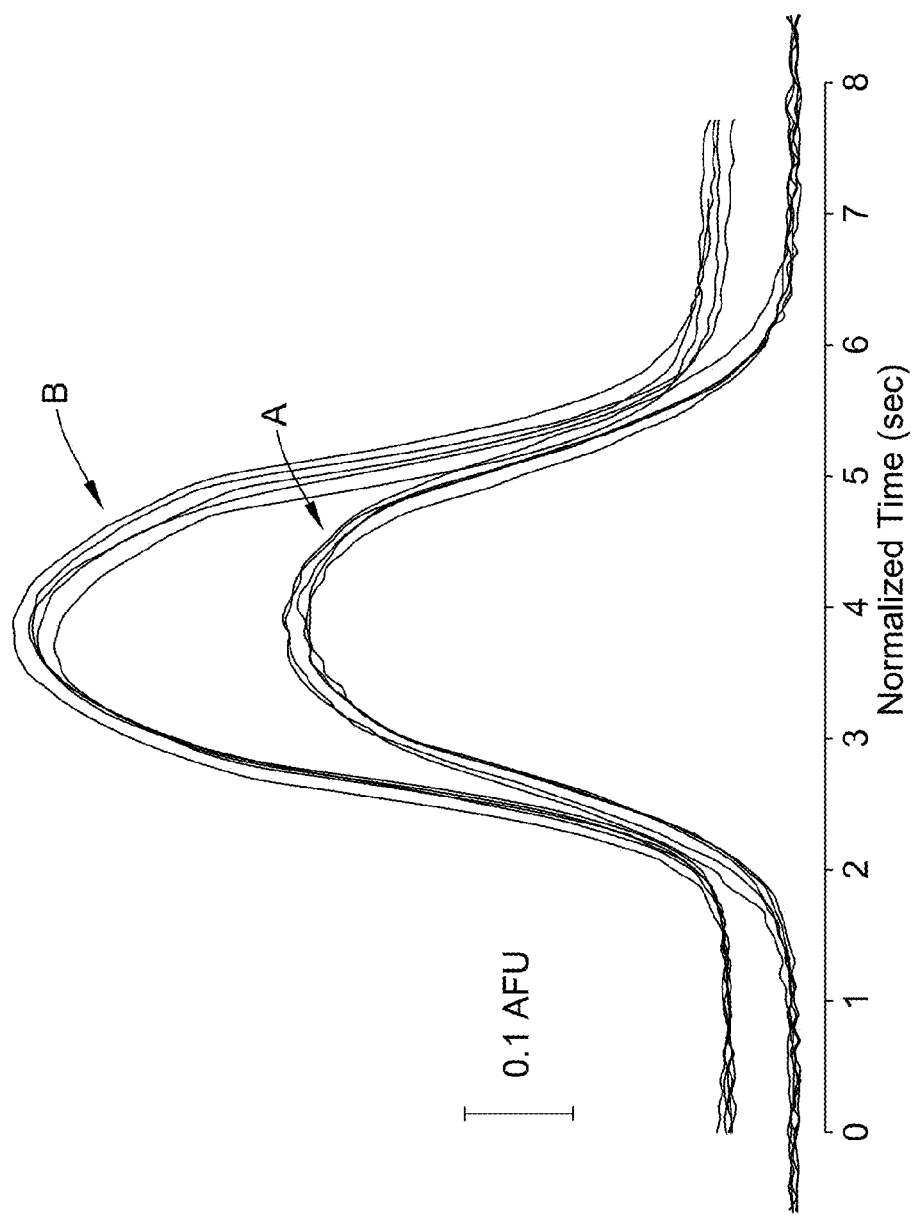
FIG. 4 is a graph illustrating the results of flow injection experiments for, with an overlay of 5 injection and detection events by the on-capillary detection (A) and the fluorescence signal with the on-chip detection (B), as described in Example 1.

FIG. 4 illustrates the results of this experiment, with an overlay of 5 injection and detection events for each method. The group of lines identified by "A" represent the fluorescence signal with the on-capillary detection and the group of lines identified by "B" represent the fluorescence signal with the on-chip detection after transfer from the fluidic tubing.

TABLE 1

| Flow injection analysis. | | |
|---|---|---|
|  | Average Peak Width (½ height) | Average Skew (10% height) |
| Capillary | 2.4 ± 0.1 s | 1.03 ± 0.09 |
| Chip | 2.3 ± 0.1 s | 1.17 ± 0.06 |

Very little band broadening occurred during the transfer from the capillary to the microfluidic devide. Analyses of these peaks showed no statistical difference (as tested by a t-test at the 95% confidence level) between the peak width at half-height for the capillary (A) and the on-chip (B) measurements (FIG. 4). There was a statistical difference (as tested by a t-test at the 95% confidence level) between the average peak skew values (measured at 10% of the peak height) (p-value=0.0202); however, there was just a very slight increase in the peak skew (40.14). Very little band broadening occurred during the transfer of analyte bands from the capillary onto the microfluidic device having the encapsulated fluidic tubing.

Example 2

Droplet Transfer Studies

Droplet studies were performed using a microfluidic device having an encapsulated 150 mm-i.d. PFA fluidic tubing in a polystyrene base layer and a reversibly sealed PDMS microchannel-forming layer having a 100 μm×65 μm microchannel positioned over the fluidic tubing i.d. Droplets were generated using a 150 mm-i.d. T-junction (commercially available from Valco, Houston, Tex.) with perfluorodecalin (PFD) was used as the carrier phase and fluorescein in water as the aqueous phase. For volume studies, two videos were recorded, one of the droplets in-tubing and one of droplets after they had been transferred on-chip. Images from each video were then used to determine the droplet size. Desegmentation studies were performed by creating an air/water interface at a channel intersection. As shown in FIGS. 5E and 5F, to create the air/water interface, the fluidic tubing was inserted into a vial that was connected to a water aspirator to create a vacuum. Water was inserted into one reservoir of the device, with the other remaining open to air. A corona discharge unit fitted with a fine tip electrode (model ETP BD-20, commercially available from Electrotechnic Products, Inc., Chicago, Ill.) was used to treat the air channel, making it hydrophilic (with the water-containing channel remaining hydrophobic). PFD/fluorescein droplets created off-chip in the 150 μm-i.d. T-junction were then introduced via the fluidic tubing, with droplet desegmentation achieved at the interface.

Figure 5A:
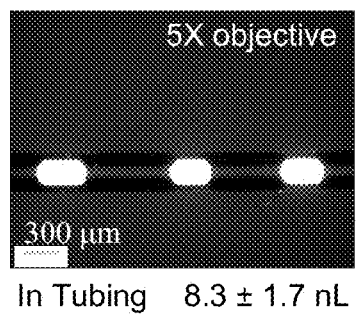
FIGS. 5A and 5B are images showing droplet transfer using a microfluidic device of the present disclosure with encapsulated tubing illustrating droplets in PFA tubing and in the microchip after transfer, respectively, as described in Example 2.
Figure 5B:
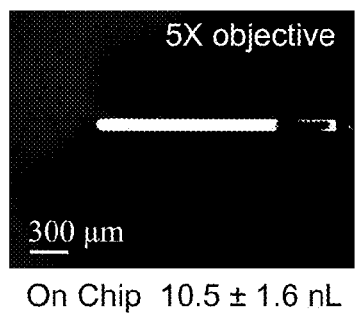
Figure 5C:
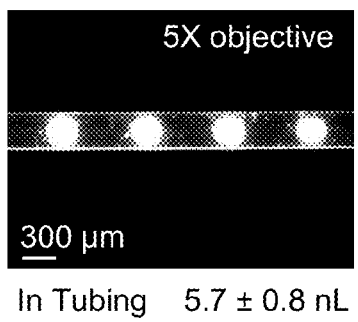
FIGS. 5C and 5D are images showing droplet transfer using microfluidic devices with inserted tubing illustrating droplets in PFA tubing and in the microchip after transfer, respectively, as described in Example 2.
Figure 5D:
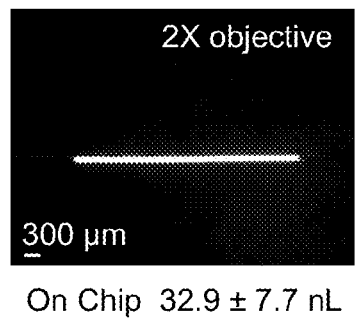
Figure 5E:
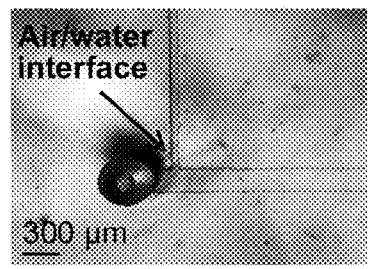
FIGS. 5E and 5F are images of an exemplary desegmentation design using a microfluidic device of the present disclosure with encapsulated tubing, illustrating an air/water interface before corona treatment (E) and after treatment (F), respectively, with droplets being desegmented at the interface.
Figure 5F:
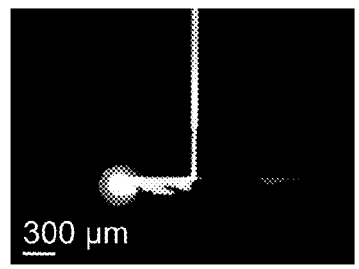

In this example, and as shown in FIGS. 5A-5D, droplets were generated off-chip using a T-junction, PFD as the carrier fluid, and fluorescein in water as the aqueous phase. A comparison was made between microfluidic devices having encapsulated fluidic tubing and microfluidic devices having inserted fluidic tubing by analyzing the droplet volume both in tubing as well as on-chip post-transfer. For the devices with encapsulated fluidic tubing, the average droplet volumes were 8.3±1.7 nL in-tubing and 10.4±1.6 nL on-chip after transfer (FIGS. 5A and 5B). This implied an average coalescence of 1.25 droplets during the transfer from the fluidic tubing to the microchip. A similar coalescence value (1.0) was observed by comparing the droplet frequency both in-tubing and on-chip. The devices with inserted fluidic tubing, however, showed a great deal of droplet coalescence. As shown in FIGS. 5C and 5D, the average droplet volume in-tubing was 5.7±0.8 nL, while once it was transferred on-chip many droplets converged, and the average droplet volume was 32.9±7.7. This implied an average coalescence of 5.77 droplets in devices with inserted fluidic tubing. The low dead volume nature of devices with encapsulated fluidic tubing enabled droplets to be transferred from off-chip processes.

One issue with using droplets is that some techniques such as electrochemistry and electrophoresis require the removal of the non-conductive carrier phase prior to analytical measurement. As shown in FIGS. 5E and 5F, by applying a vacuum to a vial in which the encapsulated PFA fluidic tubing inlet was placed, an air water interface was created in a PDMS microchip. In this case, a polystyrene base was used, with water and air being pulled through their respective reservoirs to the chip intersection and through the fluidic tubing. By applying the corona discharge to the air reservoir, that channel was rendered hydrophilic. FIG. 4F illustrates that when the segmented flow encountered the hydrophobic/hydrophilic intersection only the aqueous (fluorescein) phase entered the hydrophilic channel, with the PFD remaining in the hydrophobic channel.

Due to the robust nature of the encapsulated tubing, this microfluidic device can be used for integrating electrochemical detection or electrophoresis for droplet analysis. The use of droplets generated off-chip and then transferred to the microchip for analysis can be helpful in conserving concentration changes that occur in methods such as microdialysis sampling and also to couple different separation modes. However, low dead volume fluid connections of the devices formed by encapsulating fluidic tubing can ensure that droplets do not merge or coalesce during the microchip transfer.

Example 3

Microchip-Based Flow Analysis

In this example, microchip-based flow injection analysis was used to compare the devices that also included electrodes. Devices were created with encapsulated fluidic tubing and with inserted fluidic tubing, as described above. For off-chip injections, a 4-port injection valve fitted with a 200 nL rotor was used (Vici Rotor, commercially available from Valco Instruments, Houston, Tex.). A TES (N-[tris(hydroxymethyl)methyl]-2-aminoethanesulfonic acid (Sigma-Aldrich, St. Louis, Mo.) buffer flow stream was continuously pumped with a PHD 2000 syringe pump (Harvard Apparatus, Holliston, Mass.) through the valve at 2.0 µL/min to the flow microchannel sealed over the electrode. The analyte syringe was connected to the 4-port valve with a 75 µm i.d. fluidic tubing using a finger tight PEEK fitting and a luer adapter (Upchurch Scientific, Oak Harbor, Wash.). For the device having inserted fluidic tubing (as illustrated in FIG. 2A), the same connectors and a 50 µm i.d. fluidic tubing fitted with a 794 µm outside diameter (o.d.) microtight sleeve (Upchurch Scientific, Oak Harbor, Wash.) were used to transition from the 4-port injection valve to the microchip. For the device having encapsulated fluidic tubing (as illustrated in FIG. 1A), the encapsulated fluidic tubing was connected directly to the 4-port injection valve. Amperometric detection was achieved using a potentiostat (812B, CH Instruments, Austin, Tex.). The working electrode was a 1 mm diameter glassy carbon electrode and the counter electrode was a platinum wire inserted into the waste reservoir.

On-capillary hydrodynamic injections were made by pressurizing a vial (with helium) containing the analyte solution for a predetermined time. Two different pressure/injection time setups were used for these, with both using helium gas controlled by a regulator. One included a solenoid valve (MAC Fluid Power Engineering, St. Louis, Mo.) that was controlled with an analog power supply and timer unit (Instrument Design Lab, University of Kansas, Lawrence, Kans.). The other method utilized a Lee valve (LHDA053115H, The Lee Co, Essex, Colo.) that was integrated with a National Instruments Data Acquisition Board (National Instruments, Austin, Tex.). The acquisition board was controlled by LabView with in-house code that enabled the desired injection and run times. For either setup, a vial cap with a rubber septum as well as two vials were utilized, one with buffer and one with desired sample. The tubing from the solenoid valve was inserted through the rubber septum was used as the fluidic tubing leading to the microchip. The fluidic tubing-microchannel was first flushed with buffer for a given time by continuously pressurizing the buffer vial. An injection was achieved by pressurizing the sample vial for a given time, with this plug being moved through the system by pressuring the buffer vial using an injection pressure of 10 psi. A 1 second injection and a 26 cm (in length), 50 µm i.d. fluidic tubing at 20° C., led to an injection volume of ~40 nL. Amperometric detection was carried out as described above.

Microdialysis sampling of a concentration change was done for both devices with encapsulated features (fluidic tubing and electrodes) and devices with inserted fluidic tubing and electrodes. A 4-mm membrane brain microdialysis probe (BASi Instruments, West Lafayette, Ind.) was prepared by placing two tubing connectors (Flanged Tubing Connectors, BASi Instruments) to both inlet and outlet sides (o.d. 635 µm and i.d. 254 µm) of the probe. The probe was rinsed with water for at least 24 hours prior to the experiment. The inlet side of the probe was connected to a syringe (via a 50 µm i.d. capillary), and the outlet side was either connected to the fluidic tubing that was inserted into a PDMS microchip or to a fluidic tubing that was already encapsulated into the epoxy. In both cases, the fluidic tubing was connected to the probe was fitted with a 794 µm o.d. microtight sleeve (Upchurch Scientific, Oak Harbor, Wash.). This made a snug connection with the flanged tubing connector. A perfusate flow rate of 0.8 µl/min was used in some experiments. To stimulate a concentration change, the probe was first placed in a vial containing 1 mM fluorescein and allowed to equilibrate by reaching a steady fluorescence intensity (as measured by a fluorescence microscope described in herein). The concentration change was initiated by moving the probe to a vial containing 5 mM fluorescein for 10 seconds, after which time the probe was re-inserted into the 1 mM fluorescein vial.

In this example, microchip-based flow injection analysis using both the inserted-method device and encapsulated-method device was performed with both an off-chip injector (4-port rotary valve) and on-capillary hydrodynamic injection. A glassy carbon detection electrode was also encapsulated in the epoxy base and amperometry was used as the detection mode. A microchannel was sealed over the fluidic tubing i.d. as well as the glassy carbon electrode. It was also found that the epoxy base of the encapsulated device (which contained the tubing and electrode) could be polished each day before analysis.

In reference to FIGS. 6A-6F, catechol was used as the test analyte. In general, the most dramatic outcomes were observed with the on-capillary injection studies, where there was a much reduced injection volume (40 nL), as compared to the 4-port valve (200 nL) (see, Table 2).

TABLE 2

Peak Width measurement.

| Method | Peak Width (½ height) |
| --- | --- |
| On capillary injection with encapsulated fluidic tubing | 4.3 s |
| On capillary injection with inserted fluidic tubing | 8.5 s |
| Off-chip injection with encapsulated fluidic tubing | 9.0 s |
| Off-chip injection with inserted fluidic tubing | 24.7 s |

Considerable differences were observed in terms of peak size, shape, peak width at ½ height, and sensitivity. With on-capillary injection, the encapsulated-method device provided a peak-width at ½ height of 4.3 seconds, as compared to a 8.5 second peak-width at ½ height for the inserted-method device (FIGS. 6A and 6B). The encapsulated-method device also had more symmetrical peaks and a better sensitivity (0.5813 nA/µM vs. 0.3182 nA/µM for the inserted-method device). While less of an effect on the peak height was observed with the larger volume off-chip injection scheme, there was a significant difference between the encapsulated-method device and the inserted-method device (FIGS. 6C and 6D). With the off-chip injection, the encapsulated-method device had a peak-width at ½ height of 9.0 seconds while the inserted-method device had a much larger peak-width ½ height of 24.7 seconds.

In this example final flow analysis was determined using a microdialysis probe. A microdialysis probe was affixed to fluidic tubing that was either encapsulated into an epoxy base or inserted into the microchannel-forming layer. The probe was perfused at 0.8 μL/minute. To simulate a concentration change, the microdialysis probe was moved from a vial of 1 mM fluorescein to a vial containing 5 mM fluorescein for 10 seconds, followed by it being inserted back into the 1 mM fluorescein vial. For the encapsulated-method device, the average lag time was 87.7 seconds and the average peak width at 10% height was 94.7 seconds, while the inserted-method device demonstrated an average lag time of 93.3 seconds and an average peak width at 10% height of 120.7 seconds. The effect of the lower dead volume of the device with an encapsulated fluidic tubing connection was not as dramatic as with the microchip-based flow injection studies, primarily due to dilution effects in the relatively large volume commercially-available probe as well as the microconnectors used to transition from the probe to the fluidic tubing. However, the device with encapsulated fluidic tubing with microdialysis sampling resulted in a more dramatic response to the concentration change as compared to the device with inserted fluidic tubing.

Example 4

Conventional Capillary Electrophoresis (CE)

In this example, for the CE experiments, on-capillary hydrodynamic injections were made as described above with a solenoid valve and analog power supply and timer unit controls the solenoid valve. However, the vial cap had a platinum wire inserted through the septum. This wire was connected to a 30 kV power supply (Glassman High Voltage, Inc., Whitehouse Station, N.J.). The CE experiments used a 50 μm i.d. fused silica capillary. While the injection volume was not the same in all experiments, a typical injection pressure was approximately 2.5 psi. A 50 cm capillary and a 0.5 second injection (at 20° C.) led to an injection volume of ~3 nL. This volume could be tuned by changing the injection pressure or time. The palladium decoupler served as the electrophoretic ground (cathode). Amperometric detection was performed using a CH Instruments potentiostat. The working electrode was platinum, and a platinum wire served as the counter electrode. The buffer was 25 mM boric acid (pH 9.2). Samples were prepared by dissolving analytes in water followed by dilution to the desired concentration in electrophoresis buffer. Between each electrophoresis run, the capillary was flushed for 4 min with buffer. Prior to use, the buffer was degassed for 10 min with helium gas at 2.5 psi.

For the palladium microchip studies, a device having an 8-cm capillary (50 μm i.d.) encapsulated in epoxy was used. A PDMS microchannel was sealed over the capillary i.d. and a 1 mm palladium decoupler. For the capillary comparison studies, the capillary outlet was inserted into a separate buffer vial, with a platinum wire (inserted through the vial septum) being connected to ground. To measure the electrophoretic current as a function of the applied separation voltage, a 1 MΩ resistor was connected in series between the ground and either the palladium decoupler (for chip studies) or the platinum wire (for straight capillary studies). A voltmeter was used to measure the voltage drop across the resistor and the current was calculated from this value. The high voltage was increased in 800 V increments. The electrophoresis buffer was 25 mM boric acid (pH 9.2).

Some methods for coupling conventional CE (using fused silica capillaries) with electrochemical detection involved the use of a bare fracture decoupler, where a fused silica capillary was fractured and placed in a vial so that electrophoretic voltage can be grounded through the fracture but analyte bands are pushed through the remaining capillary and detected with electrodes inserted into the capillary outlet. While effective, these systems are homemade in nature, require a good deal of expertise to create, and, as opposed to fluorescence and absorbance detection for CE, have yet to be commercialized.

Since the microfluidic device having encapsulated fluidic tubing resulted in a low dead volume interconnect that can also be integrated with electrodes, the microfluidic device allows for the integration of conventional CE with electrochemical detection. Use of encapsulated palladium electrodes provided an effective method for decoupling the separation voltage from the detector by providing a path to ground before the detection electrode and absorbing the resulting hydrogen that was produced from the electrolysis of water at the cathode.

Figure 7A:
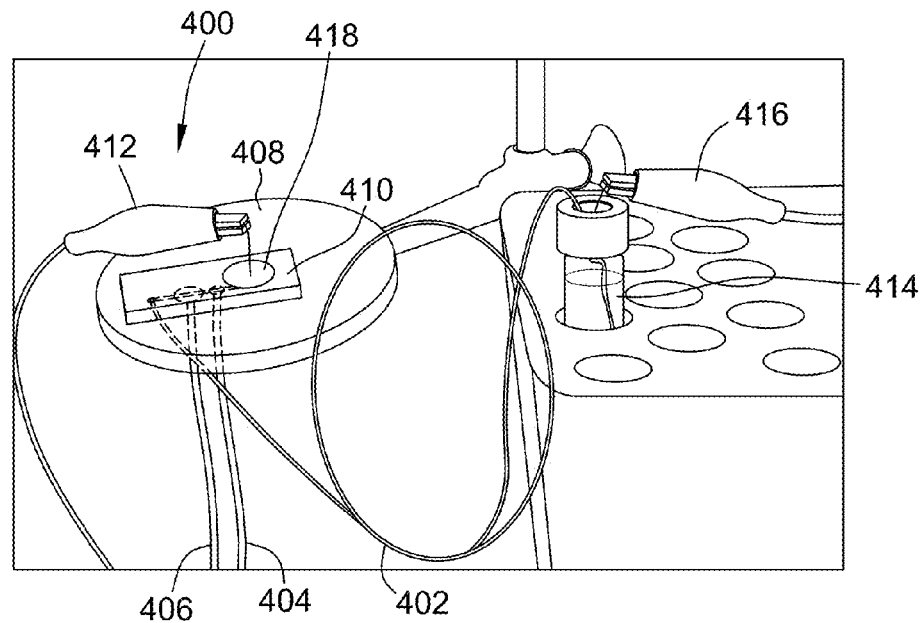
FIG. 7A is an illustration images showing a microfluidic device of the present disclosure including an encapsulated fused-silica capillary coupled in flow communication with an anodic buffer reservoir, an encapsulated platinum electrode and an encapsulated palladium decoupler all encapsulated within the base layer, a PDMS microchannel layer with a microchannel and a platinum counter electrode, as well as a high voltage source connection, as described in Example 4.
Figure 7B:
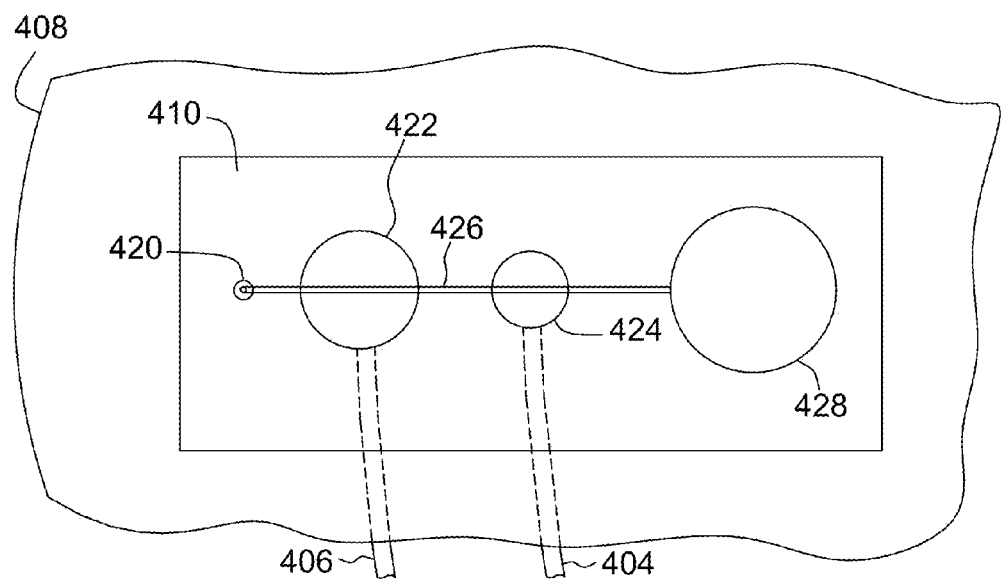
FIG. 7B is a top view illustration of the PDMS microchannel layer of FIG. 7A.
Figure 7C:
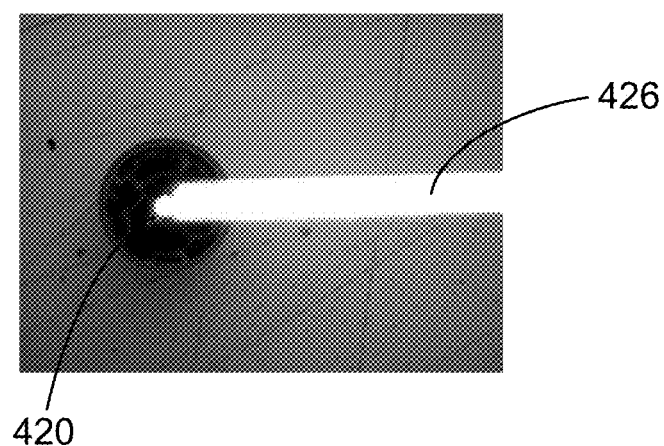
FIG. 7C is an image illustrating a close-up view of a capillary-microchannel interface of the microchip shown in FIGS. 7A and 7B, as described in Example 4.

FIG. 7A-7C show an example of a microfluidic device of the present disclosure for integrating conventional CE with electrochemistry. The microfluidic device 400 was prepared by encapsulating a fluidic tubing 402, a 0.5 mm diameter platinum detector electrode (working) 424 in FIG. 7B and a 1 mm diameter palladium decoupler (ground) electrode 422 in FIG. 7B in an epoxy base layer 408. FIG. 7A shows the lead 404 of the platinum detector (working) electrode 424 in FIG. 7B and the lead 406 of the palladium decoupler (ground) electrode 422 in FIG. 7B. The microfluidic device 400 also included a PDMS microchannel-forming layer 410 that included a straight microchannel (see, microchannel 426 in FIG. 7B) and a reservoir (418 in FIG. 7A and 429 in FIG. 7B). The microfluidic device 400 included platinum counter electrode 412 that was inserted through the PDMS microchannel-forming layer 410 and into the reservoir (418 in FIG. 7A and 429 in FIG. 7B). The distal end of the fluidic tubing 402 was inserted into an anodic buffer reservoir 414 and a high voltage connector 416 supplied the electrophoresis voltage. As shown in FIG. 7B, which is a top view of the microfluidic device 400 shown in FIG. 7A, the opening defining the inside diameter 420 of the fluidic tubing (402 in FIG. 7A), the palladium decoupler (ground) electrode 422 and the platinum detection (working) electrode 424 are substantially aligned with the straight microchannel 426 of the microchannel-forming layer 410. As shown in FIGS. 7B and 7C, the microchannel 426 was used to interface the fluidic tubing 402 with the palladium decoupler 422 and platinum detection electrode 424. As shown in FIG. 7C, after a hydrodynamic injection was made, the electrophoresis voltage was applied and analyte bands electrophoresed through the opening defining the inside diameter 420 of the fluidic tubing 404 and were transferred into the microchannel 426 where the voltage was grounded by the palladium decoupler electrode 422. The analyte band then passed over the platinum detection electrode 424 before exiting the microchannel 426 to an outlet reservoir (not visible 7C) that also contained the platinum counter electrode 412.

Figures 8A, 8B:
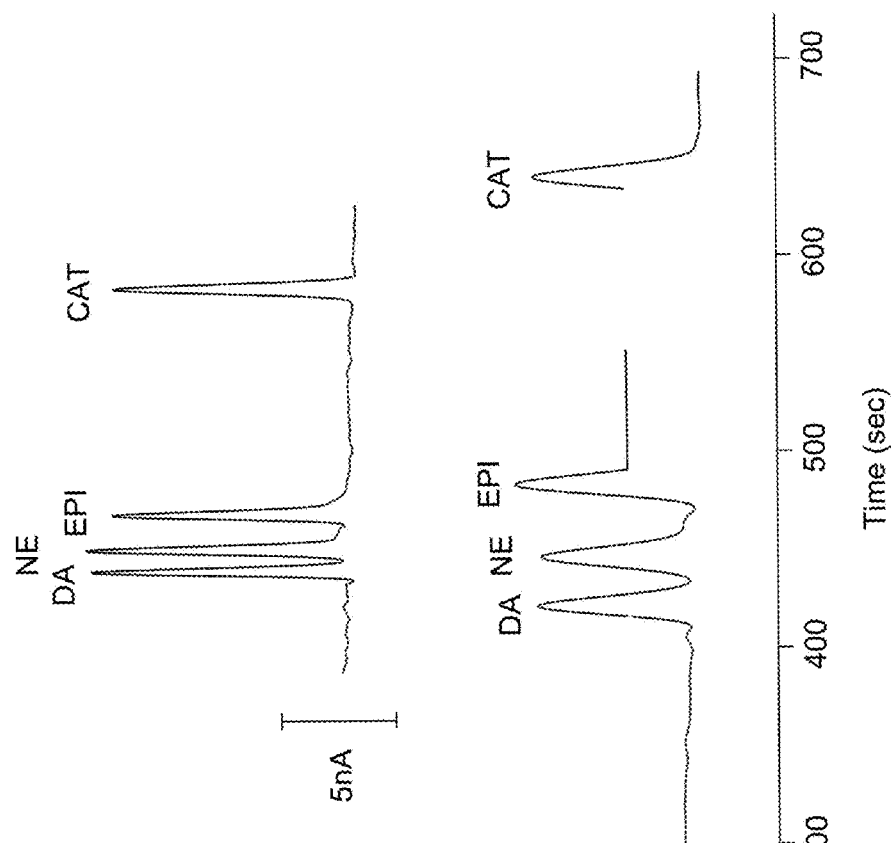
FIG. 8A is a graph illustrating the effect of microchannel cross-sectional area on the separation of dopamine (DA), norepinephrine (NE), epinephrine (EPI), and catechol (CAT) using a microfluidic device of the present disclosure having a 75 μm×25 μm microchannel cross-section, as described in Example 4.
FIG. 8B is a graph illustrating the effect of microchannel cross-sectional area on the separation of dopamine (DA), norepinephrine (NE), epinephrine (EPI), and catechol (CAT) using a microfluidic device of the present disclosure having a 100 μm×65 μm microchannel cross-section, as described in Example 4.

FIGS. 8A and 8B show the effect of the PDMS interfacing microchannel size on the electrophoresis separation. Specifically, FIGS. 8A and 8B show the separations of dopamine, norepinephrine, epinephrine, and catechol (100 μM each) using two different microchannel dimensions and a field strength of 200 V/cm. A smaller interfacing microchannel (75 µm×25 µm) resulted in an improved performance, with 45,000 theoretical plates for dopamine, 36,000 theoretical plates for norepinephrine, 40,700 theoretical plates for epinephrine, and 42,000 theoretical plates for catechol (FIG. 8A). A 100 µm×65 m microchannel resulted in 16,500 theoretical plates for dopamine, 15,800 theoretical plates for norepinephrine, 13,600 theoretical plates for epinephrine, and 21,400 theoretical plates for catechol (FIG. 8B). The improved performance can be explained by the cross-sectional area of the 75×25 µm microchannel (1875 µm$^2$) more closely matching the 50 µm fluidic tubing (1962.5 µm$^2$), with the larger microchannel 100 µm×65 µm (6500 µm$^2$) resulting in significant band broadening after the transfer to the microchannel. The Ohm's Law study was also carried out, with a straight 50 µm i.d. fluidic tubing that was grounded in a buffer vial showed similar trends as an encapsulated 50 µm i.d. fluidic tubing with a 75×25 µm interfacing microchannel and a palladium decoupler ground. In both, non-linear behavior occurred at field strengths greater than 600 V/cm.

Figure 9A:
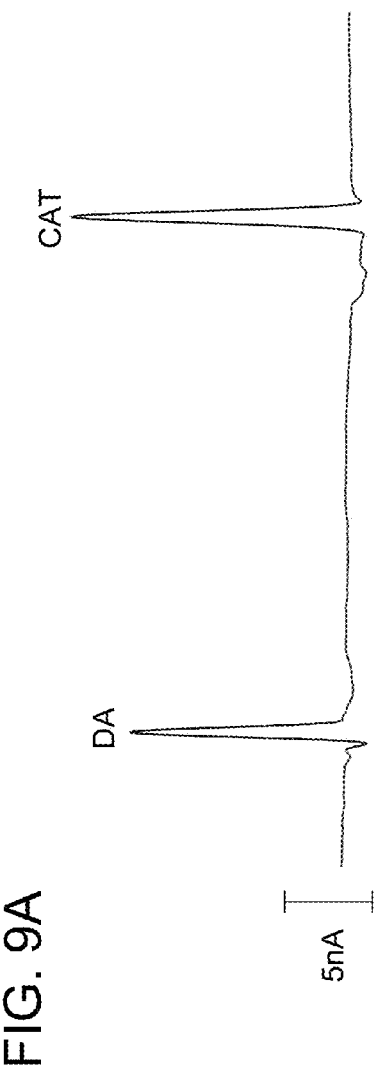
FIG. 9A is a graph illustrating the effect of field strength on the separation of dopamine (DA) and catechol (CAT) using a microfluidic device of the present disclosure and field strength of 400 V/cm, as described in Example 4.
Figure 9B:
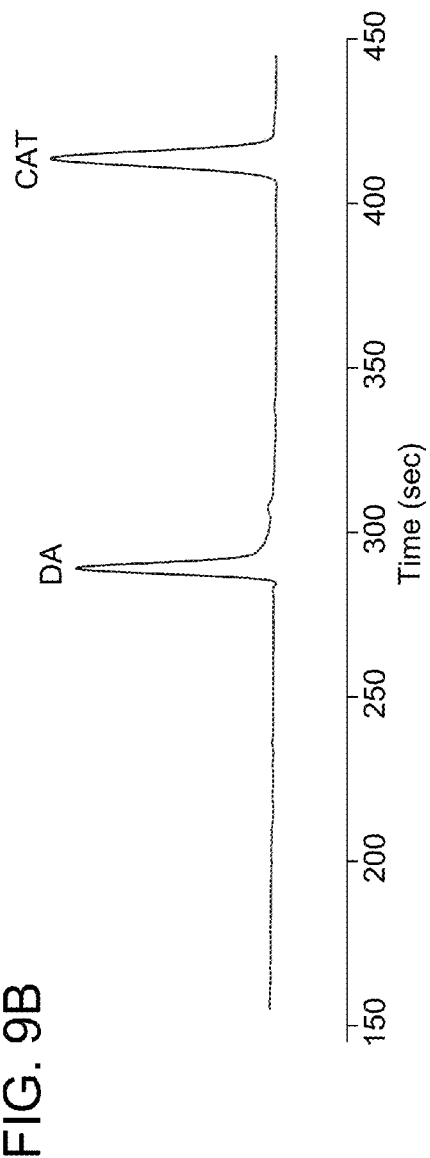
FIG. 9B is a graph illustrating the effect of field strength on the separation of dopamine (DA) and catechol (CAT) using a microfluidic device of the present disclosure and field strength of 200 V/cm, as described in Example 4.

As shown in FIGS. 9A and 9B, the effect of field strength on a separation was investigated using the 75×25 µm interfacing microchannel. A field strength of 200 V/cm yielded 39,000 theoretical plates for dopamine and 36,600 theoretical plates for catechol (FIG. 9B). Increasing the field strength resulted in an improved separation performance, with 400 V/cm giving 75,000 theoretical plates for dopamine and 55,000 theoretical plates for catechol (FIG. 9A). The limit of detection for this example was approximately 740 nM. In some experiments, a 3 nL injection volume was used. Using a smaller injection volume (0.5 nL) with a field strength of 200 V/cm also resulted in an improved separation performance, with the number of theoretical plates for dopamine and catechol being 128,600 and 91,000, respectively. Thus, devices with encapsulated capillary and electrodes are an effective method to couple conventional CE with electrochemical detection. As opposed to other devices used for decoupling methods, the alignment of tubing and electrodes remained fixed, reproducible and reusable. The device can also be disassembled and polished reused.

Example 5

Rise Time Study Using Capillary Loop Microfluidic Devices

In this example, fused silica capillaries (either 75 µm i.d. or 50 µm i.d.) were integrated into polystyrene base layers with integrated electrodes in a manner similar to the straight capillary described previously (see FIG. 3 for a schematic of the capillary loop microdevice setup used for the capillary loop experiments). The capillary loop microfluidic devices were used in rise time studies to determine successful sample transfer and analysis.

Figure 10:
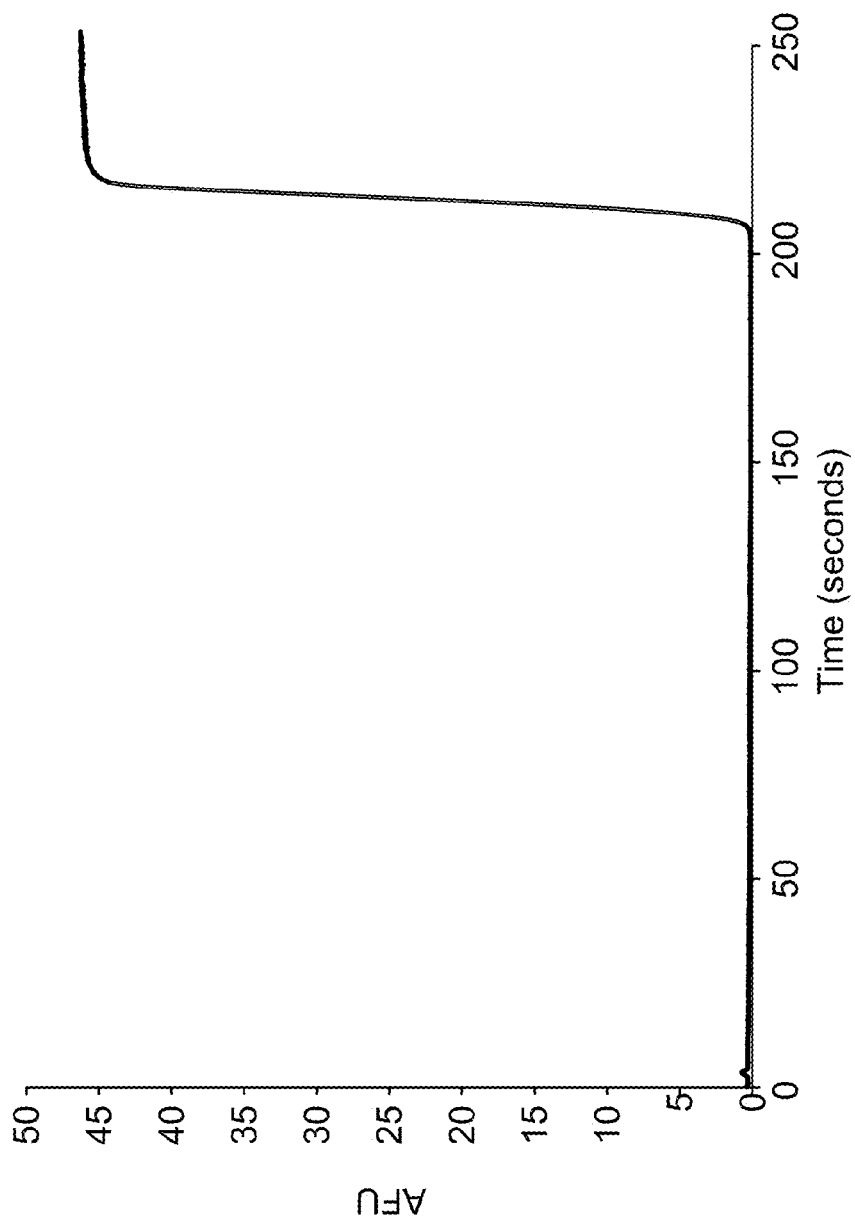
FIG. 10 is a graph illustrating rise time for on-chip fluorescence detection with the capillary loop device of the present disclosure, as described in Example 5.

To ensure successful sample transfer and fast analysis through the encapsulated capillary loop, a rise time study was first performed (see FIG. 10). This study used two 80 µm (in width)×20 µm straight channels that were sealed over the i.d. of each end of the capillary loop. The reservoir before the loop was filled with a 500 µM fluorescein in 25 mM boric buffer sample and 6000V was applied using a high voltage supply. The reservoir past the loop was grounded and filled with 25 mM boric buffer. The rise time was recorded on the straight channel past the capillary loop using fluorescence detection.

As shown in FIG. 10, a lag time of 207 seconds was recorded while the actual rise time was 6.6 seconds. The apparent mobility of fluorescein was also calculated giving a value of 2.00×10$^{-4}$ cm$^2$/V*sec. This was compared to literature values, which closely correspond (3.45×10$^{-4}$ cm$^2$/V*sec). This demonstrates that the microchannel layer/capillary interface had no significant band broadening.

Example 6

Electrophoretic Pinched Injections Using Capillary Loop Microfluidic Devices

In this example, electrophoretic pinched injections were performed using an 80 µm (in width)×20 µm microchip pinched injection design (see, FIG. 3). The pinched design portion of the microchannel layer was sealed over the capillary i.d. before the capillary loop (at the output end of the capillary loop where the capillary loop was connected to the base layer) while the straight microchannel was sealed over the capillary loop past the loop (at the input end of the capillary loop where the capillary loop reconnected in the base layer) and over the palladium decoupler electrode and platinum wire working electrode. To fill the microchannel intersection with sample, high voltage (HV) (+700 V) was applied to the buffer and sample reservoirs with the sample waste reservoir and decoupler at ground. Injections occurred by applying HV (+3000 V) to the buffer reservoir, a fraction of the HV (+2600 V) to the sample and sample waste reservoirs, and keeping the decoupler at ground. A LabSmith HVS448 3000 V High Voltage Sequencer with eight independent HV channels (LabSmith, Livermore, Calif., USA) was used as the electrophoresis voltage source. Amperometric detection was done using a CH Instruments potentiostat (812B, Austin, Tex., USA). The working electrode was platinum, and a platinum wire served as the counter electrode. The buffer used was 25 mM boric acid (pH 8.2). Samples were prepared by dissolving analytes in water followed by dilution to the desired concentration in electrophoresis buffer.

Figure 11:
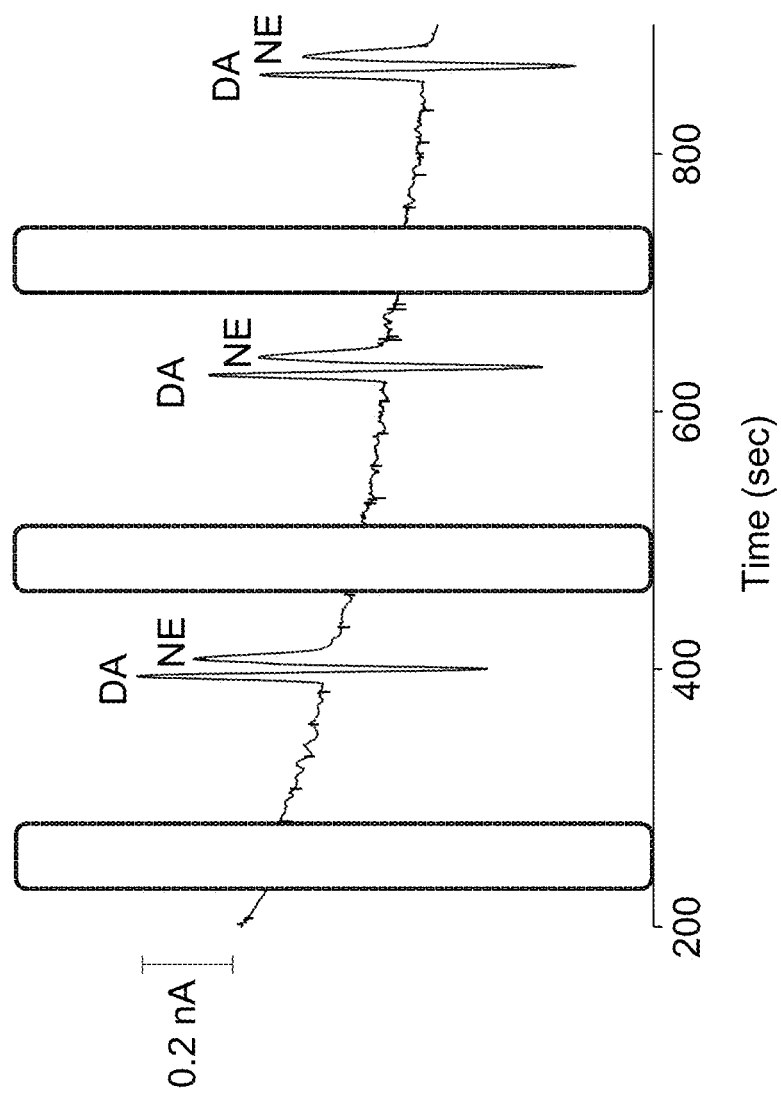
FIG. 11 is a graph illustrating chip-to-chip microchip electrophoresis separation of dopamine (DA) and norepinephrine (NE) (100 μM each) using a pinched injection scheme with three injections with the capillary loop device of the present disclosure, as described in Example 6.

FIG. 11 shows a separation of dopamine (DA) and norepinephrine (NE) (100 µM each) using the capillary loop microfluidic device with a pinched injection scheme. For 20 second fill times with 210 second separation times, up to 2,000 theoretical plates were obtained for dopamine. These results provide proof of concept that the capillary loop microfluidic device allows microchip based separations with significantly increased separation length. In addition, this type of approach can be used to interface a microchip-based separation with a capillary separation in a manner where a 2-dimensional separation is carried out.

Example 7

Interfacing Microfluidic Devices with Mass Spectrometry

Mass spectrometry (MS) is one of the most widely used analytical techniques for bioanalysis because it is highly sensitive, can determine compound structure, purity, composition, and highly accurate molecular weight. Coupling microfluidics to MS has gained much attention recently due to the ability of carrying out multiple processes on chip in a high throughput manner and then transferring them to the MS for in-depth analysis. Currently, the most popular microchip/MS interface is through electrospray ionization (ESI) because of their similar flow rates and the ability to do online transfer. The major challenge of coupling microfluidics to ESI-MS is to create a stable and efficient interface. Most of the work has focused on three different ways of developing the chip-ESI-MS interface; (1) the creation of a Taylor cone at the edge of the microchip (with a side channel used to provide the electrical connection) and spraying directly off the chip, (2) spraying from a capillary inserted into the microchip, and (3) development of ESI types that are fabricated directly on the chip. The disadvantage to the first is the large droplet formation that occurs from the Taylor cone, compromising the previous analysis steps on the chip. The weakness to the second is the dead volume that results from inserting the capillary into the chip. The chip-integrated ESI-tip has shown a lot of promise, but holds intensive fabrication procedures.

Thus, in this example, the microfluidic devices of the present disclosure having the encapsulated electrode and fluidic tubing were interfaced with ESI-MS.

Figure 12A:
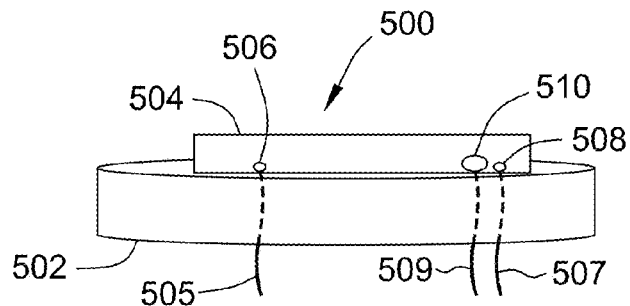
FIG. 12A is a translucent schematic illustration of an assembled microfluidic device of the present disclosure for interfacing the microfluidic device to a mass spectrometer for mass spectrometric detection, as described in Example 7.
Figure 12B:
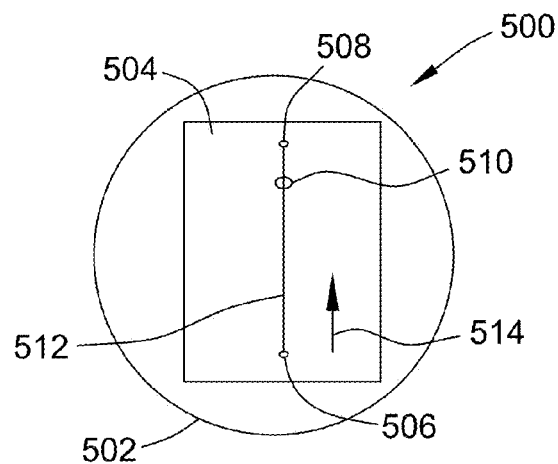
FIG. 12B is a top view of a schematic illustrating the microfluidic device of FIG. 12A, as described in Example 7.
Figure 12C:
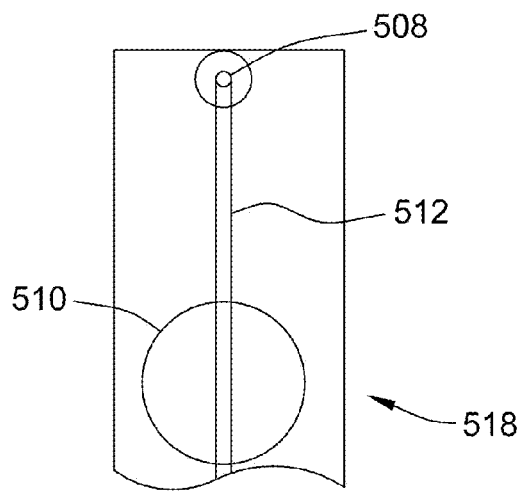
FIG. 12 C is an enlarged top view of the schematic of FIG. 12B showing the alignment of the opening of the fluidic tubing from the microfluidic device to the mass spectrometer, the microchannel and the palladium electrode, as described in Example 7.

As illustrated in FIG. 12A, a microfluidic device 500 having a base layer 502 and a microchannel-forming layer 504 was prepared according to the methods described herein. The base layer 502 included an encapsulated first fluidic tubing 505, an encapsulated second fluidic tubing 507 and an encapsulated palladium electrode 510. The microchannel-forming layer 504 included a straight microchannel 512. The arrow 514 shows the direction of the fluid flow in the straight microchannel 512. The first fluidic tubing 505 served as a sample input capillary and the second fluidic tubing 507 served as a connection to the mass spectrometer (not shown in FIG. 12). The opening 506 defining the inside diameter of the first fluidic tubing 505 and the opening 508 defining the inside diameter of the second fluidic tubing 507 leading to the MS were aligned with the microchannel 512 and the palladium electrode 510 (see also, FIG. 12B showing an enlarged image of the opening 508 defining the inside diameter of the fluidic tubing 507 interfaced with the base layer 502). The opening 506 defining the inside diameter of the first fluidic tubing 505 and the opening 508 defining the inside diameter of the second fluidic tubing 507 leading to the MS and the palladium electrode 510 were substantially coplanar with the top surface of the base layer 502. As illustrated in FIG. 12C, the microchannel 512 and the palladium electrode 510 are also substantially aligned such that the microchannel 512 passes over the palladium electrode 510 (see FIG. 12C cut-away illustration 518 of the microchannel-forming layer 504). The microfluidic device 500 also included a second electrode (not shown in FIG. 12) used to introduce pressure-based flow (via a syringe pump and injector) and a third electrode (not shown in FIG. 12) having a pulled tip (1-3 µm at the tip) to interface with the mass spectrometer. The on-chip encapsulated palladium electrode 510 was used to provide the ESI voltage source via coupling through lead 509. The encapsulated second fluidic tubing 507 provided a low dead volume transfer from the microfluidic device 500 to the MS. At the end of the second fluidic tubing distal to the microfluidic device 500, a fine tip was pulled (as is typical with capillary inlets for MS) with a $CO_2$ laser-based micropette puller (Sutter Instrument Company). This design provided a simple but low dead volume method to interface microfluidic device processes to MS detection.

This microfluidic device-ESI-MS interface was characterized with microchip-based flow injection analysis using a 5 mM ammonium formate buffer (pH=7.5). A Thermo LTQ XL linear ion trap mass spectrometer was used for all of the studies.

Figure 13A:
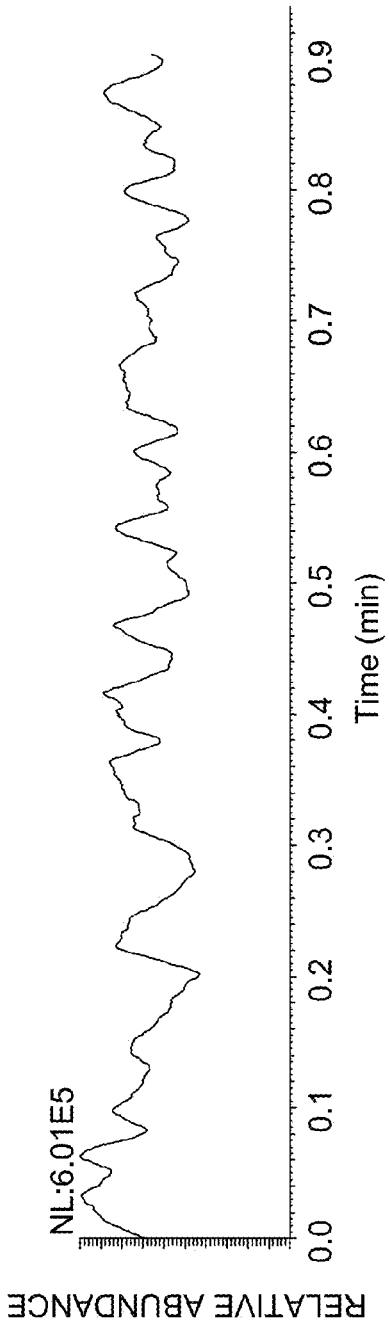
FIG. 13A is a graph showing a comparison of directly infusing caffeine into the mass spectrometer from a microfluidic device interfaced with the mass spectrometer at a flow rate of 1 μL/min and spray voltage of +4.5 kV using the on-chip electrodes for application of the ESI voltage, as described in Example 7.
Figure 13B:
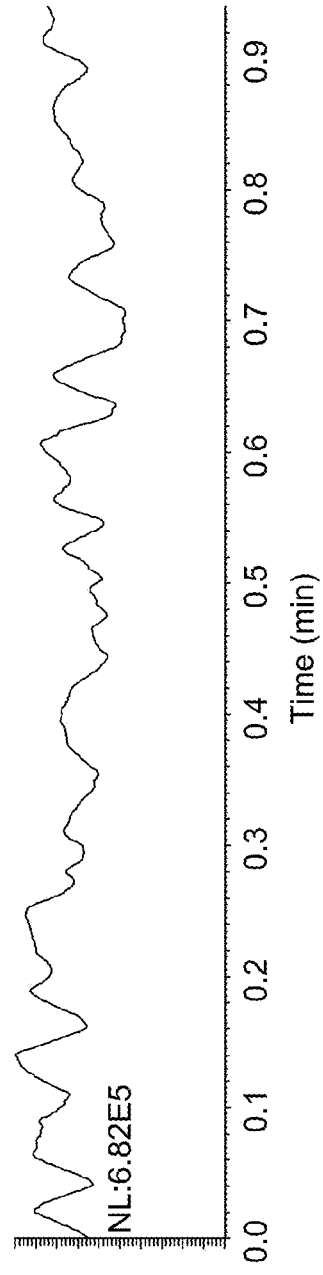
FIG. 13B is a graph showing a comparison of directly infusing caffeine into the mass spectrometer from a microfluidic device interfaced with the mass spectrometer at a rate of 150 nL/min and a spray voltage of +3.8 kV using the on-chip electrodes for application of the ESI voltage, as described in Example 7.
Figure 13C:
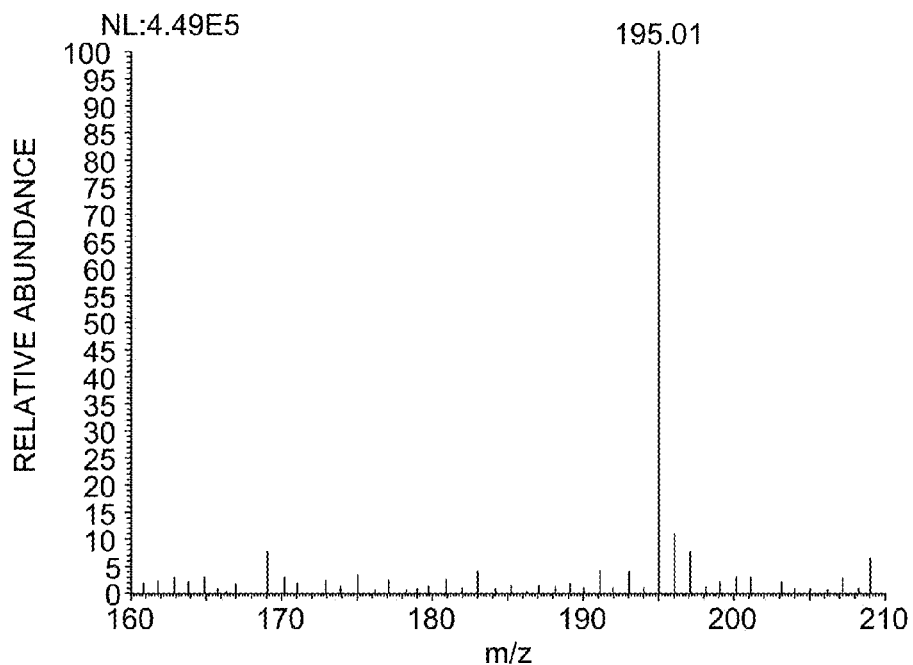
FIG. 13C is a graph of the mass spectra of caffeine (m/z=195) corresponding to direct infusion of FIG. 13A, as described in Example 7.
Figure 13D:
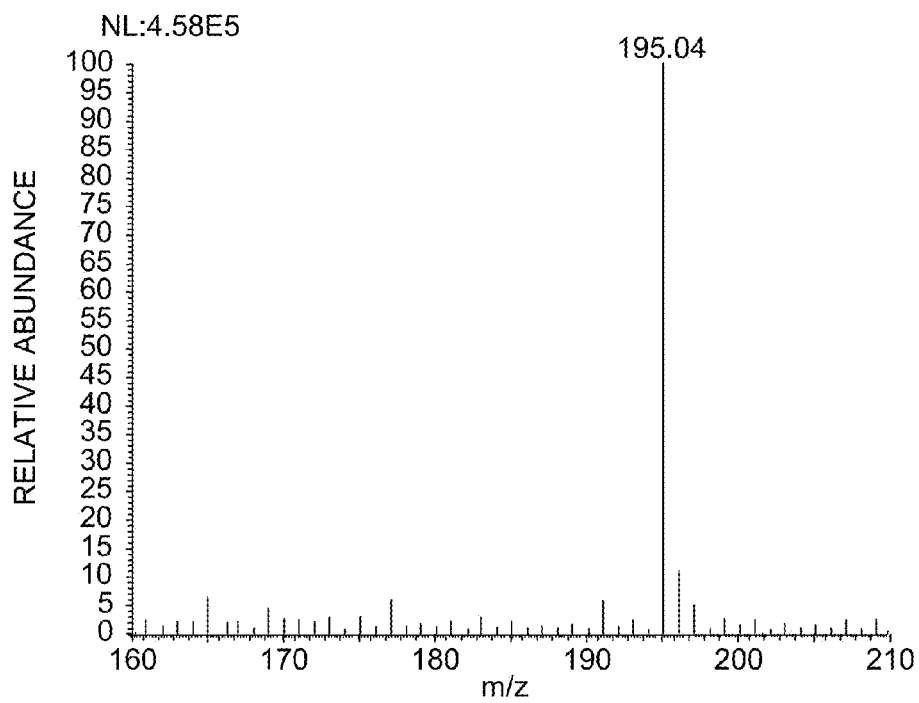
FIG. 13D is a graph of the mass spectra of caffeine (m/z=195) corresponding to direct infusion of FIG. 13B, as described in Example 7.

A flow rate comparison of 1 µL/min (see, FIG. 13A) and 150 nL/min (see, FIG. 13B) was conducted. The spray voltage for 1 µL/min was +4.50 kV and for 150 nL/min was +3.80 kV. Caffeine was directly infused into the device using a syringe pump. As shown in FIGS. 13A and 13B, both flow rates had a stable flow as a function of time. Caffeine (m/z=195) was detected at both flow rates (see, FIGS. 13C and 13D).

Example 8

Microfluidic Devices Interfaced with MS Detection

In this example, ornithine injections were performed using a Rheyodyne 6-port injection valve. The sample loop was 27 nL in volume. 50 µM ornithine at a flow rate of 1 µL/min was injected (see, FIG. 14A). Three consecutive injections were performed to demonstrate reproducibility. Running the MS in positive mode the spray voltage applied to the palladium electrode was +2.5 kV.

Figure 14B:
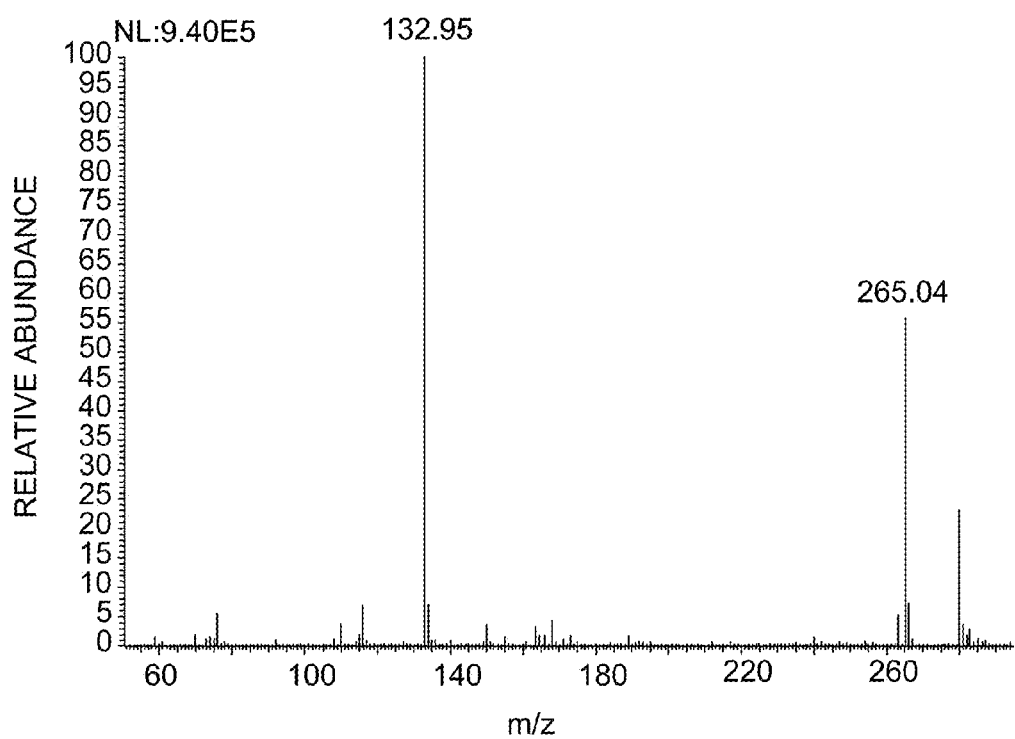
FIG. 14B is a graph of the mass spectra of ornithine in peak #1 of the graph shown in FIG. 14A and showing the ornithine dimer at 265 m/z, as described in Example 8.

Ornithine was detected, not only as a monomer (m/z=133), but also as a dimer (m/z=265) (see, FIG. 14B). The dimer consists of two ornithines with a +1 charge. As demonstrated by this example, the ESI was stable and reproducible. While these studies demonstrated the ability to use microfluidic devices having encapsulated electrodes and fluidic tubing to interface microchip systems with MS detection, this approach can also be used to integrate capillary electrophoresis (CE) with MS detection, using the encapsulated electrode to both decouple the separation voltage and provide the ESI voltage source.

The experiments described above demonstrate that devices with encapsulated fluidic tubing, along with other components such as electrodes, can lead to low dead volume interconnects. The devices also advantageously allow for a fixed alignment between the encapsulated fluidic tubing and electrodes. Additionally, the base layer can be polished. In some embodiments, the microchannel-forming layer can be removed, resealed and reusable. Because the device features such as fluidic tubing and electrodes are encapsulated in the rigid base layer, fluid interconnects remain fixed. Additionally, when soft microchannel-forming layers are used, the fluidic tubing cannot damage the soft materials that can result in leakage or failure of the microfluidic device. The fluidic tubing will also remain fixed in position and cannot be pushed into the microchannel or withdrawn from the microchannel and/or base layer as the result of incidental contact. The devices described herein, when compared to devices having inserted fluidic tubing that exhibited fluidic interconnects with an appreciable dead volume, resulted in an improved analytical performance for the integration of several off-chip analytical methods including droplet transfer and microchip-based flow analysis. These devices can also be used to integrate conventional CE with electrochemical detection, with up to 128,000 theoretical plates for dopamine being obtained. The fluidic tubing and electrodes are advantageously housed in a rigid base layer, which resulted in extremely robust devices that will be of interest to researchers wanting to develop microchips for use by non-experts.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A microfluidic device comprising:
   a base layer, wherein the base layer comprises
      an encapsulated fluidic tubing,
      at least one encapsulated electrode, and
      at least one encapsulated lead,
      wherein an opening defining an inside diameter of the encapsulated fluidic tubing and the at least one encapsulated electrode are substantially coplanar with a top surface of the base layer; and
   a microchannel-forming layer, wherein the microchannel-forming layer comprises
      at least one microchannel having a first end and a second end; and
      at least one reservoir at the second end of the at least one microchannel;
   wherein the encapsulated fluidic tubing, the at least one encapsulated electrode, the at least one microchannel and the at least one reservoir are in fluid connection and configured to channel fluid from the first end of the at least one microchannel to the reservoir; and
   wherein the opening defining an inside diameter of the encapsulated fluidic tubing is proximate to and centered with the first end of the at least one microchannel; and
   wherein a portion of the electrode and the opening of the fluidic tubing is exposed to the at least one microchannel.

2. The microfluidic device of claim 1, wherein the base layer comprises a material selected from the group consisting of epoxy, polystyrene, polycarbonate, polyester, polymethylmethacrylate, thermoset polyester, polyurethane-methacrylate cyclic olefin copolymer, polyvinylchloride, polyethyleneterephthalate glycol, polyethyleneterephthalate and combinations thereof.

3. The microfluidic device of claim 1, wherein the microchannel-forming layer comprises a material selected from the group consisting of polydimethylsiloxane, epoxy, polystyrene, polycarbonate, polyester, polymethylmethacrylate, thermoset polyester, polyurethane-methacrylate cyclic olefin copolymer, polyvinylchloride, polyethyleneterephthalate glycol, polyethyleneterephthalate and combinations thereof.

4. The microfluidic device of claim 1, wherein the fluidic tubing is selected from the group consisting of a fused silica capillary, a polyetheretherketone (PEEK) tubing, a perfluoroalkoxy (PFA) tubing, a fluorinated ethylene propylene (FEP) tubing, a stainless steel tubing, an ethylene-chlorotrifluoroethylene tubing, a tygon tubing, a thermoplastic elastometer polypropylene tubing, a polyphenylsulfone tubing, an ethylene-tetrafluoroethylene tubing and combinations thereof.

5. The microfluidic device of claim 1, wherein the at least one electrode is selected from the group consisting of a palladium electrode, a platinum electrode, a gold electrode, a mercury-modified gold electrode, a glassy carbon electrode, and a carbon fiber electrode, a nickel electrode, a mercury-modified platinum electrode, a mercury-modified palladium electrode, a carbon paste electrode, a silver electrode, a copper electrode, a graphite electrode, a titanium electrode, a chromium electrode, a mixed metal oxide electrodes, a carbon nanotube-containing electrode, an Indium tin oxide electrode and combinations thereof.

* * * * *